United States Patent [19]
Crowl et al.

[11] Patent Number: 5,869,233
[45] Date of Patent: Feb. 9, 1999

[54] ACQUIRED IMMUNE DEFICIENCY SYNDROME (AIDS) VIRAL ENVELOPE PROTEIN AND METHOD OF TESTING FOR AIDS

[76] Inventors: Robert M. Crowl, 115 Anderson Pkwy., Cedar Grove, N.J. 07009; Robert C. Gallo, 8513 Thornden Ter., Bethesda, Md. 20817; E. Prem Reddy, 547 Atterbury Rd., Villanova, Pa. 19085; George M. Shaw, 3571 Rockhill Rd., Birmingham, Ala. 35223; Flossie Wong-Staal, 3 Lynn Manor Ct., Rockville, Md. 20850

[21] Appl. No.: 456,352

[22] Filed: Jun. 1, 1995

Related U.S. Application Data

[62] Division of Ser. No. 132,406, Oct. 6, 1993, and Ser. No. 811,896, Dec. 20, 1991, and a continuation of Ser. No. 224,590, Sep. 13, 1988, and Ser. No. 725,021, Apr. 19, 1985.

[51] Int. Cl.⁶ .............................. C12Q 1/70; C12P 21/00; C12N 15/49; C07H 21/04
[52] U.S. Cl. ..................... 435/5; 435/69.1; 435/320.1; 530/300; 530/350.1; 536/23.1
[58] Field of Search ................ 435/5, 7, 320.1, 435/240.1, 69.1, 188.1; 530/350; 536/23.1

[56] References Cited

U.S. PATENT DOCUMENTS

| | | | |
|---|---|---|---|
| 4,237,224 | 12/1980 | Cohen et al. | 435/69.1 |
| 4,304,863 | 12/1981 | Colins et al. | 435/172.3 |
| 4,520,113 | 5/1985 | Gallo et al. | 435/5 |
| 4,629,783 | 12/1986 | Cosand | 530/324 |
| 4,725,669 | 2/1988 | Essex | 530/322 |
| 4,743,678 | 5/1988 | Essex | 530/35 |
| 5,156,949 | 10/1992 | Luciw | 435/5 |

FOREIGN PATENT DOCUMENTS

| | | |
|---|---|---|
| 51705/85 | 12/1984 | Australia . |
| 152 030 | 8/1985 | European Pat. Off. . |
| 173 529 | 3/1986 | European Pat. Off. . |
| 181 150 | 5/1986 | European Pat. Off. . |
| 201 716 | 11/1986 | European Pat. Off. . |
| 84/04327 | 11/1984 | WIPO . |
| 86/02383 | 4/1986 | WIPO . |

OTHER PUBLICATIONS

Casadaban et al., J. Mol. Biol. 138:179 (1980).
Chang et al., Biotechnology 3:905 (1985).
Chang et al., Science 228:93 (1985).
Crowl et al., Cell 41:979 (1985).
Crowl et al., Gene 38:31 (1985).
Muesing et al., Nature 313:450 (1985).
Ratner et al., Nature 313:277 (1985).
Sarngadharan et al., Science 224:506 (1984).
Schupbach et al., Science 224:503 (1984).
Shaw et al., Science 226:1165 (1985).
Pauletti et al., Anal. Biochem. 151:540 (1985).
Veronese et al., Science 229:1402 (1985).
Sanchez–Pescador, Science 227:484–492 (1985).
Barre Sinoussi et al., Science 220:868–871 (1983).
Montagnier et al., Human T–Cell Leukemia/Lymphoma Virus, Cold Spring Harbor, N.Y. pp. 363–379 (1984).
Alizon et al., Nature 312:757–759 (1984).
Wain–Hobson et al., Cell 40:9–17 (1985).
Shoeman et al., Chapter 6 in HIV Detection by Genetic Engineering Methods (ed. Luciw and Steimer) pp. 99–119 (1989).
Lomedico, et al., Letters to Nature 312:458–462 (1984).
Lacal, et al., Proc. Natl. Acad. Sci., 81:5305–5309 (1984).
Budiansky, Nature 312:583 (1984).
Kiyokawa, et al., Proc. Natl. Acad. Sci., 81:6202–6206 (Oct. 1984) "Envelope proteins of human T–cell leukemia virus: Expression in *Escherichia coli* and its application . . . ".

*Primary Examiner*—Michael P. Woodward
*Assistant Examiner*—Mary K. Zeman
*Attorney, Agent, or Firm*—Morgan & Finnegan, L.L.P.

[57] ABSTRACT

An envelope protein of the etiologic agent of acquired immune deficiency syndrome (AIDS) and a method for its preparation are disclosed. Proviral DNA is transferred into a host cell after engineering into an expression vector which produces the envelope protein. A method of testing human blood for the presence of antibodies to the AIDS virus using the AIDS envelope protein is disclosed.

26 Claims, 14 Drawing Sheets

```
              1                                                    50
HXB-3    MRVKEK-----YQHLWRWGWRWGTMLLGMLMICSATEKLWVTVYYGVPVWKEATT
BH-10
BH-8                                                          F
LAV                     K       I
ARV-2        K   --GTREN        ---- -                 -      --

51                                                   100
HXB-3    TLFCASDAKAYDTEVHNVWATHACVPTDPNPQEVVLVNVTENFNMWKNDM
BH-10
BH-8
LAV
ARV-2                R                         G          N 101                                                  150
HXB-3    VEQMHEDIISLWDQSLKPCVKLTPLCVSLKCTDLKNDTNTNSS-----SGRMIME
BH-10
BH-8
LAV                                    G A       NTNSS   E M
ARV-2        Q                      T N G A      NWKEEI------

151                                                  200
HXB-3    KGEIKNCSFNISTSIRGKVQKEYAFFYKLDIIPIDND--TTSYTLTS---CNTSV
BH-10
BH-8             K
LAV
ARV-2            T    D I  N L RN VV    AST N  NYRLIH   R 201                                                  250
HXB-3    ITQACPKVSFEPIPIHYCAPAGFAILKCNNKTFNGTGPCTNVSTVQCTHG
BH-10
BH-8
LAV                                   A
ARV-2                  T              K
```

FIG. 2A

```
               251                                                    300
      HXB-3    IRPVVSTQLLLNGSLAEEEVVIRSVNFTDNAKTIIVQLNTSVEINCTRPN
      BH-10                          A              Q
      BH-8                                          D
      LAV                            A              Q
   5  ARV-2            I             D   N          E  A 301                                                    350
      HXB-3    NNTRKKIRIQRGPGRAFVTIGKIGNMRQ-AHCNISRAKWNATLKQIASKLR
      BH-10          S                                   N     D
      BH-8                                                     D
  10  LAV            S
      ARV-2          S Y --       H  T R  IGDIRK        Q  N   E   VK 351                                                    400
      HXB-3    EQFGNNKTIIFKQSSGGDPEIVTHSFNCGGEFFYCNSTQLFNSTWFNSTW
      BH-10
  15  BH-8
      LAV
      ARV-2             V N          M    R       T       N  -RLNH 401                                                    450
  20  HXB-3    STEGSNNTEGSDTITLPCRIKQFINMWQEVGKAMYAPPISGQIRCSSNIT
      BH-10        K              I
      BH-8         K              I
      LAV
      ARV-2    -   --- K N    I   I                       G    S 451                                                    500
  25  HXB-3    GLLLTRDGG-NNNNGSEIFRPGGGDMRDNWRSELYKYKVVKIEPLGVAPTK
      BH-10             - S   E
      BH-8              - S   E
      LAV               -                              --
      ARV-2             T VT DT V                         I    I 30
               501                                                    550
      HXB-3    AKRRVVQREKRAVGI-GALFLGFLGAAGSTMGAASMTLTVQARQLLSGIVQ
      BH-10                   -
      BH-8                    -
      LAV                     -                R
  35  ARV-2                   V  M                V L
```

FIG. 2B

```
           551                                                    600
    HXB-3  QQNNLLRAIEAQQHLLQLTVWGIKQLQARILAVERYLKDQQLLGIWGCSG
    BH-10                G
    BH-8
    LAV
    ARV-2                                       V        R 601                                                    650
    HXB-3  KLICTTAVPWNASWSNKSLEQIWNHTTWMEWDREINNYTSLIHSLIEESQ
    BH-10                           NM
    BH-8                            NM
    LAV                             NM
    ARV-2                  D      DNM      Q E    D    NT YT 651                                                    700
    HXB-3  NQQEKNEQELLELDKWASLWNWFNITNWLWYIKLFIMIVGGLVGLRIVFA
    BH-10
    BH-8
    LAV                                                I
    ARV-2                                    S         I 701                                                    750
    HXB-3  VLSVVNRVRQGYSPLSFQTHLPIPRGPDRPEGIEEEGGERDRDRSIRLVN
    BH-10
    BH-8        I                    N
    LAV         I                    -
    ARV-2       I             R  V         D                V  D 751                                                    800
    HXB-3  GSLALIWDDLRSLCLFSYHRLRDLLLIVTRIVELLGRRGWEALKYWWNLL
    BH-10
    BH-8
    LAV
    ARV-2       F     E         R          AA T  I    H       S 801                                                    850
    HXB-3  QYWSQELKNSAVSLLNATAIAVAEGTDRVIEVVQEAYRAIRHIPRRIRQG
    BH-10                                                     G
    BH-8              N                        L  A
    LAV                                                       G C
    ARV-2       I        W        T               A R      L  H
```

HXB-3    LERILL
   BH-10
   BH-8
   LAV
5  ARV-2    L

" ---- " designates a deletion
```

FIG. 2D

```
                                                                    METArg
    ValLysGluLysTyrGlnHisLeuTrpArgTrpGlyTrpArgTrpGlyThrMETLeuLeuGlyMETLeu
    METIleCysSerAlaThrGluLysLeuTrpValThrValTyrTyrGlyValProValTrpLysGluAla
    ThrThrThrLeuPheCysAlaSerAspAlaLysAlaTyrAspThrGluValHisAsnValTrpAlaThr
    HisAlaCysValProThrAspProAsnProGlnGluValValLeuValAsnValThrGluAsnPheAsn
    METTrpLysAsnAspMETValGluGlnMETHisGluAspIleIleSerLeuTrpAspGlnSerLeuLys
    ProCysValLysLeuThrProLeuCysValSerLeuLysCysThrAspLeuLysAsnAspThrAsnThr
    AsnSerSerSerGlyArgMETIleMETGluLysGlyGluIleLysAsnCysSerPheAsnIleSerThr
    SerIleArgGlyLysValGlnLysGluTyrAlaPhePheTyrLysLeuAspIleIleProIleAspAsn
    AspThrThrSerTyrThrLeuThrSerCysAsnThrSerValIleThrGlnAlaCysProLysValSer
    PheGluProIleProIleHisTyrCysAlaProAlaGlyPheAlaIleLeuLysCysAsnAsnLysThr
    PheAsnGlyThrGlyProCysThrAsnValSerThrValGlnCysThrHisGlyIleArgProValVal
    SerThrGlnLeuLeuLeuAsnGlySerLeuAlaGluGluGluValValIleArgSerValAsnPheThr
    AspAsnAlaLysThrIleIleValGlnLeuAsnThrSerValGluIleAsnCysThrArgProAsnAsn
    AsnThrArgLysLysIleArgIleGlnArgGlyProGlyArgAlaPheValTh

AMINO ACID DISTRIBUTION

| Name | Number of Residues |
|---|---|
| A-Alanine | 47 |
| B-Aspartic Acid-Asparagine | 0 |
| C-Cysteine | 21 |
| D-Aspartic Acid | 27 |
| E-Glutamic Acid | 49 |
| F-Phenylalanine | 26 |
| G-Glycine | 58 |
| H-Histidine | 14 |
| I-Isoleucine | 63 |
| K-Lysine | 44 |
| L-Leucine | 83 |
| M-Methionine | 17 |
| N-Asparagine | 60 |
| P-Proline | 29 |
| Q-Glutamine | 42 |
| R-Arginine | 52 |
| S-Serine | 57 |
| T-Threonine | 60 |
| V-Valine | 56 |
| W-Tryptophan | 31 |
| Y-Tyrosine | 20 |
| Z-Glutamine-Glutamic Acid | 0 |

FIG. 6B

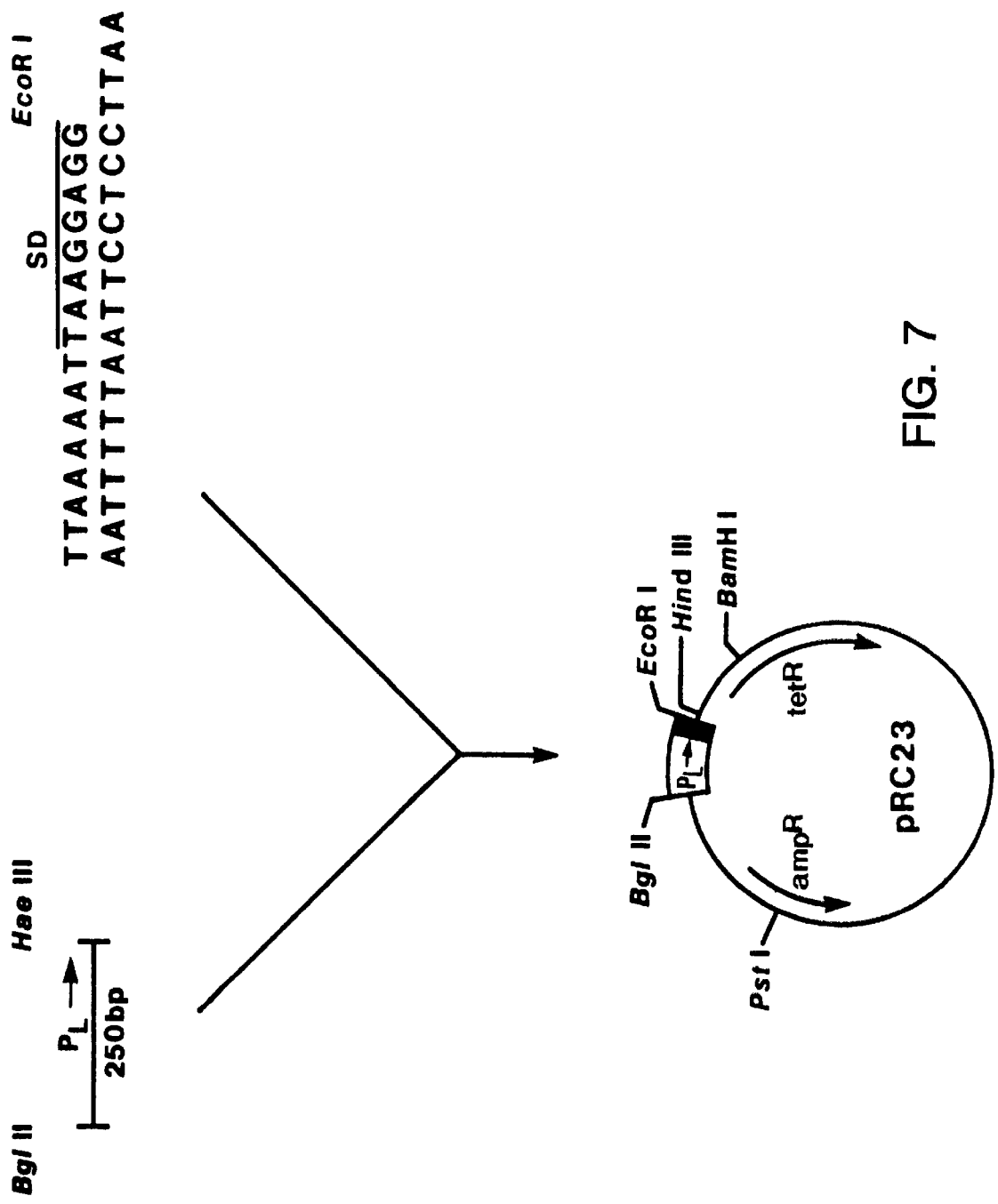

ACQUIRED IMMUNE DEFICIENCY SYNDROME (AIDS) VIRAL ENVELOPE PROTEIN AND METHOD OF TESTING FOR AIDS

This is a division of application Ser. No. 08/132,406, filed Oct. 6, 1993; and a divisional of Ser. No. 07/811,896, filed Dec. 20, 1991, and a continuation of Ser. No. 07/224,590 filed Sep. 13, 1988, and a continuation of Ser. No. 06/725,021, filed Apr. 19, 1985.

FIELD OF THE INVENTION

This invention relates to a protein, designated env AIDS, which is the viral envelope protein of the etiologic agent for acquired immune deficiency syndrome, the expression vector which encodes env AIDS, the production of env AIDS using recombinant DNA technology and a method for detecting the presence of AIDS antibodies in human blood.

BACKGROUND OF THE INVENTION

From 1981 to date, there have been eight thousand (8,000) people diagnosed as having acquired immune deficiency syndrome (AIDS). N.Y. Times, A-11 Jan. 11, 1985. AIDS has been characterized by the onset of severe opportunistic infections secondary to an effect on the body's immune system. Gottlieb, M. S. et al., Pneumocystis Carinic Pneumonia and Mucosal Candidiasis in previously healthy homosexual men: evidence of a new acquired cellular immuno-deficiency, N. Eng. J. Med. 305, 1426–1431 (1981). The disease has been found in male homosexuals, patients receiving blood products, intravenous drug addicts, and individuals originating from Haiti and Central Africa. Piot, P. et al. Acquired immunodeficiency syndrome in a heterosexual population in Zaire. Lancet 11, 65–69 (1984). The causative agent was suspected to be of viral origin as the epidemiological pattern of AIDS was consistent with a transmissable disease. At least three (3) retroviruses have been isolated from cultured T-cells of several patients with AIDS, or from white blood cells of persons at risk for the disease. A novel human retrovirus called lymphadenopathy-associated virus (LAV) was discovered and its properties were consistent with its etiological role in AIDS. That virus was isolated from a patient with lymphadenopathy and hence the name. Montagnier, L. et al. A New Human T-lymphotropic retrovirus: characterization and possible role in lymphadenopathy and acquired immune deficiency syndromes. In Human T-Cell Leukemia/Lymphoma Virus, R. C. Gallo, M. Essex and L. Gross, eds. (Cold Spring Harbor, N.Y.: Cold Spring Harbor Laboratory) pp. 363–370. Other human retroviruses, specifically two subgroups of the human T-cell leukemia/lymphoma/lymphotropic virus, types I and III have been isolated. (HTLV I: Poicsz, B. J. et al. PNAS (USA) 77, 7415 (1980)); (HTLV-III: Popovic, M. et al. Detection, isolation and continuous production of cytopathic retroviruses (HTLV-III) from patients with AIDS and pre-AIDS. Science 224, 797–500 (1984)). Still another virus, the AIDS-associated retrovirus (ARV), was proposed as the causative agent. Levy, J. A. et al. Isolation of lymphocytopathic retroviruses from San Francisco patients with AIDS. Science 225, 840–842 (1984)). Both the HTLV-III and ARV retroviruses display biological and seroeidemiological properties similar to LAV. Levy et al., supra, Popovic et al. supra. As seen from the above, at least three (3) retroviruses have been postulated as the etiologic agent or AIDS: LAV: ARV; and, HTLV subtypes I and III.

LAV, HTLV III and ARV-II genomes have been molecularly cloned. Shaw, G. M. et al., Serological analysis of a subgroup of human T-lymphotropic retroviruses (HTLV III) associated with AIDS. Science 224, 503–505 (1984). Alizon, M. et al. Molecular Cloning of lymphadenopathy—associated virus. Nature, in press. The complete nucleotide sequence of the proviral genome of LAV, ARV and HTLV III has been determined. Ratner, L. et al. Complete nucleotide sequence of the AIDS virus, HTLV III. Nature 313, 277–284 (1985); Sanchez-Pescadov, R. et al. Nucleotide sequence and expression of an AIDS-associated retrovirus (ARV-2). Science 227, 484–492 (1985); and, Wain-Hobson, S. et al. Nucleotide sequence of the AIDS virus, LAV. Cell 40, 9–17 (1985).

One reason for the difficulty in determining the etiologic agent of AIDS was due to the reactivity of various retroviral antigens with serum samples from AIDS patients. For example, serum samples from AIDS patients have been shown to react with antigens of HTLV I and HTLV III. (HTLV-I: Essex, M., et al., "Antibodies to Cell Membrane Antigens Associated with Human T-Cell Leukemia Virus in Patients with AIDS", Science 220, 859(1983)); (HTLV-III: Sarngadharan, M. G. et al., "Antibodies Reactive With Human T-Lymphotropic Retroviruses (HTLV-III) in the Serum of Patients With AIDS", Science 224, 506–508 (1984)). Envelope gene products of HTLV demonstrated antigenicities cross-reactive with antibodies in sera from adult T-cell leukemia patients. Kiyokana, T. et al. Envelope proteins of human T-cell leukemia virus: Expression in *Escherichia coli* and its application to studies of env gene functions" PNAS (USA) 81, 6202–6206 (1984). Adult T-cell leukemias (ATL) differ from acquired immune deficiency syndrome (AIDS) in that HTLV-I causes T-cell malignancies, that is uncontrolled growth of T-cell. In AIDS rather than cell growth there is cell death. In fact this cytopathic characteristic of HTLV III was critical to determining ultimately the specific retroviral origin of the disease. Thus the etiologic agent of AIDS was isolated by use of immortalized human neoplastic T cell lines (HT) infected with the cytopathic retrovirus characteristic of AIDS, isolated from AIDS afflicted patients. Seroepidemiological assays using this virus showed a complete correlation between AIDS and the presence of antibodies to HTLV III antigens. Gallo et al. supra 1984; Sarngadharan et al. supra 1984; Schupbach et al. Serological Analysis of a subgroup of human T-lymphotropic retroviruses (HTLV III) associated with AIDS, Science 224, 503–505 (1984). In addition, nearly 85% of patients with lymphadenopathy syndrome and a significant proportion of asymptomatic homosexual men in AIDS endemic areas were also found to carry circulating antibodies to HTLV III. Taken together, all these data indicate HTLV III to be the etiologic agent for AIDS.

Until the successful culturing of AIDS virus using H-9 cell line the env AIDS protein of the AIDS virus had not been isolated, characterized or synthesized. This in major part is due to the fact that the virus is cytopathic and thus isolation of the virus was not possible. Popovic, M. et al., Detection, Isolation, and Continuous Production of Cytopathic Retroviruses (HTLV III) From Patients With AIDS and Pre AIDS, Science 224, 497–500 (1984). Once the human T-cell line resistant to the cytopathic effects of the virus was discovered, a molecular clone of proviral DNA could be achieved.

The need for a sensitive and rapid method for the diagnosis of AIDS in human blood and its prevention by vaccination is very great. Virtually all the assays/tests presently available are fraught with errors. In fact the Center for Disease Control (CDC) has indicated that presently available tests be used solely for screening units of blood for antibody to HTLV III. The CDC went further by stating that the presently available ELISA tests not be used for general screening of high risk populations or as a diagnostic test for AIDS. Federal Register 50(48), 9909, Mar. 12, 1985. The errors have been traced to the failure to use a specific antigenic protein of the etiologic agent for AIDS. The previously used proteins were derived from a viral lysate. Since the lysate is made from human cells infected with the virus, i.e. the cells used to grow the virus, the lysate will contain human proteins as well as viral proteins. Thus preparation of a pure antigen of viral protein is very difficult. The antigen used produced both false positive and false negative results. Budiansky, S., AIDS Screening, False Test Results Raise Doubts, Nature 312, 583(1984). The errors caused by the use of such lysate proteins/peptides can be avoided by using a composition for binding AIDS antibodies which is substantially free of the non-AIDS specific proteins. Compositions that are substantially pure AIDS envelope protein can be used as antigens. The AIDS envelope protein of the instant invention has been established to have conserved epitopes which permit its use to screen for, diagnose and/or prevent by vaccination the AIDS virus. The instant invention demonstrates that the envelope protein with its conserved epitopes includes all the variants which have been claimed as the sole etiologic agent.

The envelope AIDS protein of the present invention may be produced by conventionally known methods. The processes by which the novel protein may be produced can be divided into three groups: (1) chemical synthesis; (2) preparation of a gene prepared by chemical synthesis is inserted into a host and a protein is produced by the host; and (3) a gene obtained biotechnically is inserted into a host and a protein is produced by the host.

In one embodiment of this invention, recombinant DNA techniques are utilized by which env AIDS DNA from a natural source is introduced into a cell to produce the env AIDS protein. One method of obtaining DNA which encodes env AIDS is to read the genetic code in reverse and synthesize an oligodioxynucleotide which should encode the env AIDS amino acid sequence. As the env protein has not been isolated or characterized this approach cannot be pursued.

Alternatively gene expression can be obtained using recombinant DNA technology if DNA isolated from natural sources is used instead of synthetic DNA.

SUMMARY OF THE INVENTION

This invention is directed to the engineering of HTLV III env gene into suitable expression vectors; transformation of host organisms with such expression vectors; and producton of envelope AIDS protein (env AIDS) by culture of such transformed cells. Another aspect of the present invention relates to the isolation and use of the resulting recombinant env AIDS protein.

Another aspect of the present invention is the identification and determination of the proviral DNA sequence. More specifically, this aspect of the invention relates to determination and comparison of the proviral nucleotide sequence of the envelope genes of the purported etiologic agent of AIDS i.e. lymphadenopathy-associated virus (LAV), AIDS-associated retrovirus (ARV) and the human T-cell leukemia/lymphoma/lymphotropic virus type III (HTLV III).

A further aspect of this invention relates to a diagnostic method for testing human blood for the presence of antibodies to the env AIDS protein. This aspect of the invention overcomes the problems of all previously used blood tests for AIDS. One of the problems is the use of compositions to bind AIDS antibody which contain proteins or peptides which were not derived solely from the AIDS etiologic agent. A composition using homogeneous envelope AIDS protein of this invention overcomes the nonspecificity of the prior tests or assays. Yet another aspect of this invention is a diagnostic method for detecting and/or determining the presence of the antigen in human blood.

Another aspect of this invention is to use the env AIDS proteins of the instant invention as antigens suitable for providing protective immunity against AIDS when incorporated into a vaccine.

BRIEF DESCRIPTION OF THE DRAWINGS

FIGS. 1A–1B. The nucleotide sequence of the envelope gene.

FIGS. 2A–2D. Comparison of the amino acid sequence of the env protein of the four purported etiologic agents of AIDS.

FIG. 6A. The amino acid sequence of the AIDS envelope protein.

FIG. 6B. The amino acid distribution of the envelope protein comprising the AIDS envelope protein.

FIG. 7. Plasmid construct pRC23 produced by inserting into pCR2 a 250 base pair BglII-HaeIII fragment containing the λ $P_L$ promoter joined to a pair of complementary synthetic oligonucleotides comprising a model ribosome binding site (RBS), (solid black region), as described in Example 2.

DETAILED DESCRIPTION OF THE INVENTION

Figure 3:
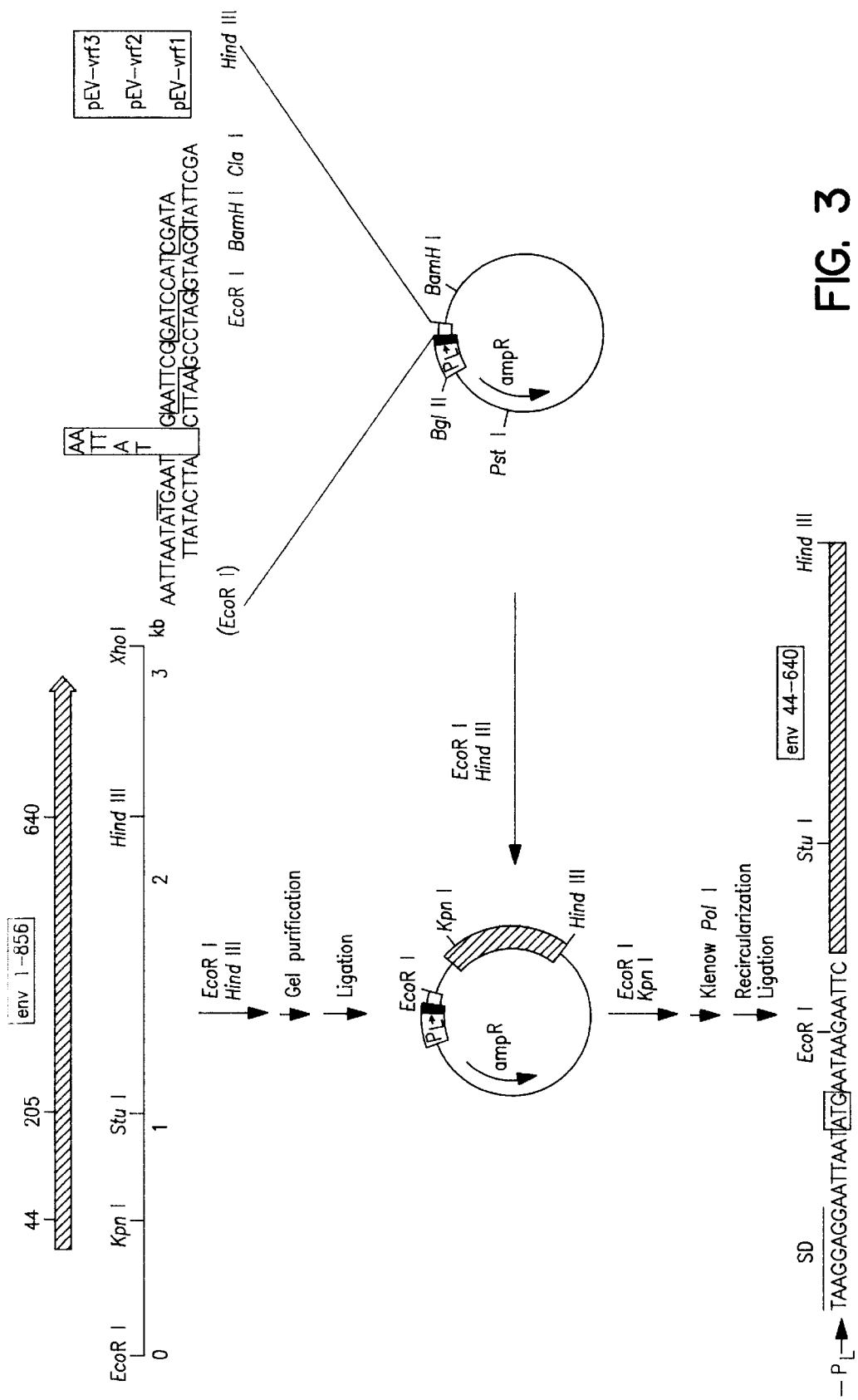
FIG. 3. Construction of the pEV/env44-640 expression plasmids. The upper left panel shows a simplified restriction site map of the 3.15 Kb EcoRI-XhoI segment of the HTLV-III genome which contains the env coding region (cross-hatched arrow). The right panel shows the structure and pertinent sequences of the pEV-vrf plasmids. The solid black region represents the synthetic ribosome binding site sequences upstream of the ATG initiation codon (overlined). See Experimental Procedures for a detailed description of the env expression plasmid constructions.

In the description the following terms are employed:

Nucleotide—A monomeric unit of DNA consisting of a sugar moiety (pentose), a phosphate, and either a purine or pyrimidine base (nitrogenous heterocyclic). The base is linked to the sugar moiety via the glycosidic carbon (1' carbon of the pentose). That combination of a base and a sugar is called a nucleoside. Each nucleotide is characterized by its base. The four DNA bases are adenine ("A"), guanine ("G"), cytosine ("C") and thymine ("T").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"). TAG, TAA and TGA are translation stop signals and ATG is a translation start signal.

Reading Frame—The grouping of codons during translation of mRNA into amino acid sequences. During translation the proper reading frame must be maintained. For example, the sequence GCTGGTTGTAAG may be translated in three reading frames or phases, each of which affords a different amino acid sequence:

GCT GGT TGT AAG—Ala-Gly-Cys-Lys

G CTG GTT GTA AG—Leu-Val-Val

GC TGG TTG TAA G—Trp-Leu-(STOP)

Polypeptide—A linear array of amino acids connected one to the other by peptide bonds between the -amino and carboxy groups of adjacent amino acids.

Genome—The entire DNA of a cell or a virus. It includes inter alia the structural genes coding for the polypeptides of the substance, as well as operator, promoter and ribosome binding and interaction sequences, including sequences such as the Shine-Dalgarno sequences.

Structural Gene—A DNA sequence which encodes through its template or messenger RNA ("mRNA") a sequence of amino acids characteristic of a specific polypeptide.

Transcription—The process of producing mRNA from a structural gene.

Translation—The process of producing a polypeptide from mRNA.

Expression—The process undergone by a structural gene to produce a polypeptide. It is a combination of transcription and translation.

Plasmid—A circular double-stranded DNA molecule that is not a part of the main chromosome of an organism containing genes that convey resistance to specific antibiotics. When the plasmid is placed within a unicellular organism, the characteristics of that organism may be changed or transformed as a result of the DNA of the plasmid. For example, a plasmid carrying the gene for tetracycline resistance (Tet$^R$) transforms a cell previously sensitive to tetracycline into one which is resistant to it. A cell transformed by a plasmid is called a "transformant".

Cloning Vehicle—A plasmid, phage DNA or other DNA sequences which are able to replicate in a host cell, which are characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and have the capacity to infect some host cell and be maintained therein.

The nomenclature used to define the peptides or proteins is that used in accordance with conventional representation such that the amino group at the N-terminus appears to the left and the carboxyl group at the C-terminus to the right. By natural amino acid is meant one of common, naturally occurring amino acids found in proteins comprising Gly, Ala, Val, Leu, Ile, Ser, Thr, Lys, Arg, Asp, Asn, Glu, Gln, Cys, Met, Phe, Tyr, Pro, Trp and His. By Nle is meant norleucine, and by Nva is meant norvaline. Where the amino acid residue has isomeric forms, it is the L-form of the amino acid that is represented unless otherwise expressly indicated. In addition, amino acids have been designated by specific letters of the alphabet such that: A-Alanine; B-Aspartic Acid-Asparagine; C-Cysteine; D-Aspartic Acid; E-Glutamic Acid; F-Phenylalanine; G-Glycine; H-Histidine; I-Isoleucine; K-Lysine; L-Leucine; M-Methionine; N-Asparagine; P-Proline; Q-Glutamine; R-Arginine; S-Serine; T-Threonine; V-Valine; W-Tryptophan; Y-Tyrosine; Z-Glutamine-Glutamic Acid.

In accordance with the present invention, the search for the envelope protein of the etiologic agent for acquired immune deficiency syndrome (AIDS) has led to the isolation and sequencing of the proviral gene of the AIDS virus. It has now been discovered, for what is believed to be the first time that the postulated etiologic agents of AIDS, lymphadenopathy-associated virus (LAV), AIDS-Associated retrovirus (ARV) and human T-cell leukemia/lymphoma/lymphotropic virus, HTLV III, are in fact variants of the same virus. For purposes of this invention and claims the virus causing AIDS will be referred to herein as AIDS virus. AIDS virus will be understood to include the variants which have been postulated as the causative agent of AIDS, namely LAV, ARV and HTLV III. The envelope protein of the AIDS virus (env AIDS) is a 97,200 dalton protein with 32 potential N-glycosylation setes. Nucleotide sequence analysis of the AIDS envelope gene of the putative etiologic agents of AIDS demonstrates that all the viruses are variants of the same virus. That is there is approximately 1 to 20% divergence or variation from the sequence of the envelope gene of HTLV III and the sequences of the envelope genes of the other viruses LAV and ARV-2. The amino acid sequence of the AIDS env protein is set forth in FIG. 6(a). The amino acid distribution is set forth in FIG. 6(b).

Figure 1A:
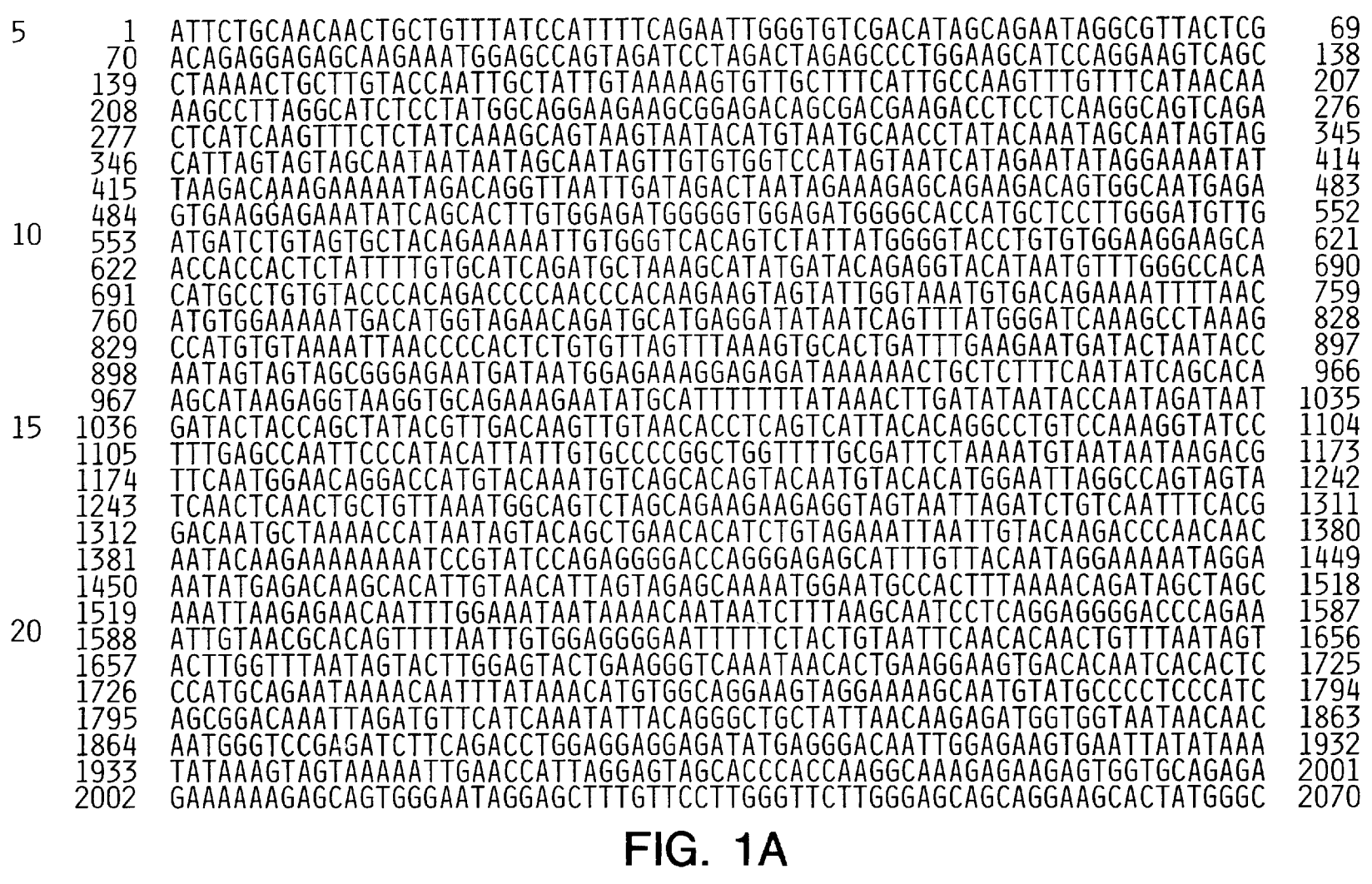

The nucleotide sequence of the envelope gene is shown in FIGS. 1A–1B. The proviral DNA sequence, using methods known to one of ordinary skill in the art such as the chemical degradation method of Maxam and Gilbert or the M13 sequencing system of Messing which is a modification of the dideoxy nucleotide chain termination method of Sanger, was analyzed to determine the location of the region coding for the envelope protein. The location of an open reading frame, i.e. a long stretch of triplet codons not interrupted by a translational stop codon, for the envelope gene was determined. The open reading frame coding for the env gene is 863 amino acids and contained an ATG codon at the eighth position from the 5' end of the reading frame. The ATG codon is known to be a universal translation-initiation codon.

The integrated proviral genome of HTLV-III was cloned from the genomic DNA of H9 cells infected with HTLV-III. Shaw et al., 1984 Molecular characterization of Human T-cell leukemia (lymphotropic) virus type III in the acquired immune deficiency syndrome. Science 226, 1165–1171 (1984). Since the HTLV-III provirus was found to lack XbaI restriction sites, a genomic library was constructed by using XbaI digested H9/HTLV-III DNA. There are several methods available to one of ordinary skill in the art for screening the bacterial clones containing the AIDS env protein cDNA. These include, for example, RNA selection hybridization, differential hybridization with a synthetic probe or screening for clones that produce the desired protein by immunological or biological assays. From the genomic library, colonies of cells transformed with DNA that contains the HTLV III sequences were selected by hybridization screening of the library with HTLV III cDNA. The DNA insert of the hybridization-positive clone, HXB-3, was excised from the plasmid DNA and sequenced.

The predicted product of the env gene shares many features in common with the envelope gene products of other retroviruses. Thus, a hydrophobic region is seen in the middle of the protein (amino acids 519–534) which includes a processing site for the cleavage of the precursor protein into exterior and transmembrane proteins. Similarly, the amino terminal end contains a short stretch of hydrophobic amino acids (amino acids 17–37) which constitutes a potential signal sequence. The HTLV-III envelope precursor differs from the other retroviral envelope protein precursors in that it contains an additional stretch of 180 amino acids at the carboxy terminus.

Polymorphism within the Envelope Region of AIDS Virus

The recent publication of the nucleotide sequences of LAV, ARV-2 and HTLV-III (Ratner et al., supra, 1985; Sanchez-Pescadov et al., supra, 1985; Wain-Hobson et al., supra, 1985) allows a detailed comparison of these various isolates obtained from AIDS patients from different parts of the world. HTLV-III clones were isolated from AIDS patient lymphocytes obtained from the east coast of the United States, while LAV was isolated from a French man and ARV was isolated from a patient in California. A comparison of the sequence data confirms the earlier observations made using restriction enzyme site analysis which showed approximately 10% variation. The present analysis shows that the various isolates show the greatest amount of conservation in the gag and pol regions while the most divergence occurs in the env region. A comparison of the four env sequences is presented in FIGS. 2A–2D. With respect to the envelope gene, HTLV-I and LAV are more closely related to each other than the ARV clone. Approximately 1.6% divergence was observed between the HTLV-III (HXB-3) and LAV sequence. Among the HTLV sequences, the divergence was about 1.6%. However, approximately 17% divergence was observed between HTLV-III and ARV-II and this was more pronounced in the extracellular region of the envelope gene product. FIG. 2. This high rate of divergence could be due to the geographical location from where the two isolates were derived or the time of isolation of these variants. ARV-2 was isolated from the west coast of the United States more recently. The HTLV-III isolates for which the nucleotide sequences have been determined were all obtained from the east coast of the United States a year earlier. LAV was obtained from a French patient who appears to have acquired the virus in New York about the same period. The observed differences in the sequence probably reflect divergent evolution of strains separated in time or geography or both. Within the env region, the highest level of divergence is in the extracellular portion of the protein.

Expression Vector

A wide variety of host/cloning vehicle combinations may be employed in cloning the double-stranded DNA. For example, useful cloning vehicles may consist of segments of chromosomal, nonchromosomal and synthetic DNA sequences, such as various known bacterial plasmids, e.g., plasmids from *E. coli* such as pBR322, phage DNA, and vectors derived from combinations of plasmids and phage DNAs such as plasmids which have been modified to employ phage DNA or other expression control sequences or yeast plasmids. Useful hosts may include microorganisms, mammalian cells, plant cells and the like. Among them microorganisms and mammalian cells are preferably employed. As preferable microorganisms, there may be mentioned yeast and bacteria such as *Escherichia Coli, Bacillus subtilis, Bacillus stearothermophilus* and Actinomyces. The above-mentioned vectors and hosts may also be employed for the production of a protein from a gene obtained biologically as in the instant invention. Of course, not all host/vector combinations may be equally efficient. The particular selection of host/cloning vehicle combination may be made by those of skill in the art after due consideration of the principles set forth without departing from the scope of this invention.

Furthermore, within each specific cloning vehicle, various sites may be selected for insertion of the double-stranded DNA. These sites are usually designated by the restriction endonuclease which cuts them. For example, in pBR322 the EcoRI site is located just outside the gene coding for ampicillin resistance. Various sites have been employed by others in their recombinant synthetic schemes. Several sites are well recognized by those of skill in the art. It is, of course, to be understood that a cloning vehicle useful in this invention need not have a restriction endonuclease site for insertion of the chosen DNA fragment. Instead, the vehicle could be joined to the fragment by alternative means.

The vector or cloning vehicle and in particular the site chosen therein for attachment of a selected DNA fragment to form a recombinant DNA molecule is determined by a variety of factors, e.g., number of sites susceptible to a particular restriction enzyme, size of the protein to be expressed, susceptibility of the desired protein to proteolytic degradation by host cell enzymes, contamination of the protein to be expressed by host cell proteins difficult to remove during purification, expression characteristics, such as the location of start and stop codons relative to the vector sequences, and other factors recognized by those of skill in the art. The choice of a vector and an insertion site for a particular gene is determined by a balance of these factors, not all selections being equally effective for a given case.

There are several Known methods of inserting DNA sequences into cloning vehicles to form recombinant DNA molecules which are equally useful in this invention. These include, for example, direct ligation, synthetic linkers, exonuclease and polymerase-linked repair reactions followed by ligation, or extension of the DNA strand with DNA polymerase and an appropriate single stranded template followed by ligation.

It should, of course, be understood that the nucleotide sequences of the DNA fragment inserted at the selected site of the cloning vehicle may include nucleotides which are not part of the actual structural gene for the desired polypeptide/protein or may include only a fragment of the complete structural gene for the desired protein. It is only required that whatever DNA sequence is inserted, a transformed host will produce a protein/peptide having an immunological activity to the AIDS env protein or that the DNA sequence itself is of use as a hybridization probe to select clones which contain DNA sequences useful in the production of polypeptides/proteins having an immunological activity to the AIDS env protein.

The cloning vehicle or vector containing the foreign gene is employed to transform a host so as to permit that host to express the protein or portion thereof for which the hybrid DNA codes. The selection of an appropriate host is also controlled by a number of factors recognized by the art. These include, for example, compatibility with the chosen vector, toxicity of proteins encoded by the hybrid plasmid, ease of recovery of the desired protein, expression characteristics, biosafety and costs. A balance of these factors must be struck with the understanding that not all hosts may be equally effective for expression of a particular recombinant DNA molecule.

A preferred embodiment of the instant invention was to express segments of the AIDS env protein in *E. coli* by inserting restriction fragments isolated from the cloned proviral genome into the versatile pEV-vrf (variable reading frame) expression plasmids (Lacal et al., Expression of Normal and Transforming H-ras Genes in *E. coli* and Purification of Their Encoded Proteins. Proc. Nat. Acad. Sci, USA 81, 5305–5309, 1984; Lomedico, P. et al., Cloning and Expression of Murine Interleukin-1 cDNA in *E. coli*, Nature 312, 458–462, 1984). Restriction fragments are fragments of proviral DNA resulting from the action of restriction enzymes. These versatile pEV-vrf plasmids are derivatives of pBR322 which contain the phage lambda P1 promoter, a synthetically-derived ribosome-binding site, and convenient cloning sites (EcoRI, BamHI, ClaI and HindIII) just downstream to the initiation codon. In the present synthesis the preferred initial cloning vehicle is the bacterial plasmid pBR322 (ATCC 37017) and the preferred initial restriction endonuclease sites therein are the EcoRI and HindIII sites. (FIG. 3). The plasmid is a small (molecular weight approximately 2.6 megadaltons) plasmid carrying a resistance gene to the antibiotic ampicillin (amp). The plasmid has been fully characterized (F. Bolivar et al., Construction And Characterization Of New Cloning Vehicles II. A Multi-Purpose Cloning System, Gene, 95–113 (1977); J. G. Sutcliffe, pBR322 Restriction Map Derived From The DNA Sequence: Accurate DNA Size Markers Up To 4361 Nucleotide Pairs Long, Nucleic Acids Research, 5, pp. 2721–28 (1978)). Insertion of the DNA product in this site provides a large number of bacterial clones each of which contains one of the proviral DNA genes or fragments thereof present in the DNA product of Hg cells. Only a very few of these clones will contain the gene for env AIDS or fragments thereof. The preferred host for initial cloning in accordance with this invention is *E. coli* MC 1061. Casadaban, M. J. and Cohen, S. N., Analysis of Gene Control Signals by DNA Fusion and Cloning *E. coli*, J. Mol. Biol., 138, 179–207, 1980. A set of three pEF-vrf plasmids was constructed to accomodate all three translational reading frames. The P1 promoter is regulated by a temperature-sensitive cI repressor encoded on the compatible plasmid pRK248cIts (ATCC 33766) (Bernard and Helinski, 1979). These expression plasmids have been used to produce substantial amounts of several heterologous proteins in *E. coli*, including v-bas p21 (Lacal et al., supra, 1984) and murine interleukin-1 (Lomedico et al., supra, 1984).

The coding sequences for amino acid residues #44 to 640 of the env protein are located downstream of the P1 promoter between the KPnI and HindIII sites on the restriction map as shown in FIG. 3. Aside from the location of these convenient restriction sites, these sequences were chosen for bacterial expression experiments because they did not include the amino-terminal signal peptide as well or the hydrophobic transmembrane segment at the carboxyl end. These sequences were excluded to avoid possible toxicity problems which can occur when hydrophobic proteins are over-produced in bacterial cells. In a preferred embodiment of this invention an expression plasmid was constructed that would direct the synthesis of this segment of the env gene product (designated pEV/env 44-640), an intermediate construction was first made by inserting a 2400 bp EcoRI-HindIII fragment between the EcoRI and HindIII sites in the pEV-vrf plasmids. The HTLV-III sequences (600 bp) between the EcoRI and the KpnI site were then removed from the intermediate construction as shown in FIG. 3. These plasmid constructions were carried out with all three pEV-vrf plasmids so that subsequent deletions could be made and the correct reading frame maintained. In addition, the constructions made in the incorrect reading frames served as important controls in the expression experiments described below.

In another embodiment of this invention, a second set of expression plasmids were constructed in a similar fashion by deleting sequences between EcoRI and StuI sites which occur 483 bp downstream to the site in the env gene. Again these deletions (designated pEV/env 205-640) were made in all three reading frames. The translation termination codon used in all of the env expression plasmids is presumably an in-frame TAA located 23 bp downstream of the HindIII site in the plasmid. Thus, 8 amino acid residues at the carboxyl terminus are encoded by pBR322.

Expression of ENV AIDS

There are several approaches to screen for bacterial clones containing env AIDS cDNA. These include, for example, RNA selection hybridization, differential hybridization, hybridization with a synthetic probe and screening for clones that produce the desired protein by immunological or biological assays. Two methods are available to screen using immunological assay: screening of bacterial colonies for the presence of protein using antibody; and, preferably, the bacterial lysates are electrophoresed, blotted onto a nitrocellulose paper and then probed with the antibody.

In a preferred embodiment of this invention, cultures of the *E. coli* strain MC 1061 transformed with pRK248cIts and the pEV 1, 2, or 3/env 44-640 (or pEV 1, 2 or 3/env 205-640) were grown in M9 medium at 30° C. to mid-log phase and then induced by shifting to 42° C. for 2 hr. Samples of the bacterial cultures were then taken and subjected to SDS-polyacrylamide gel electrophoresis, followed by Western blot analysis to detect env proteins. The protein blots were treated with antisera to env AIDS proteins isolated either from immunized rabbits or from AIDS patients previously shown to contain high titer antibodies to AIDS antigens. This was followed by incubation with $^{125}$I-labelled *Staphylococcous aureus* protein A, washing and autoradiography. Similar results were obtained with both sera except that the human serum was found to contain much higher titers of anti-HTLV-III antibodies and was devoid of all background reactivity with the *E. coli* proteins. For this reason human antibodies were used in all subsequent characterization.

FIG. 5 shows the pattern of reactivity of the env AIDS proteins synthesized in bacteria (recombinant proteins) with anti-HTLV-III antibodies. The open reading frame in pEV3/env 44-640 encodes a protein that should migrate as a 68 Kd band on the gel. In fact, a 68 Kd band is observed in the lane corresponding to the induced cells containing pEV3/env 44-640 (lane C). However, in addition to the 68 Kd band, these cells synthesized proteins of 35 Kd, 25 Kd and 18 Kd which specifically cross-reacted with anti-HTLV-III antibodies. No HTLV-III cross-reacting bands are evident in the uninduced control (Lane b) or in a second negative control sample (Lane a) of induced cells containing a plasmid that directs the synthesis of v-bas p21 oncogene product (Lacal et al., 1984). The appearance of multiple bands synthesized from the env gene sequences was an unexpected result. Another unexpected result was the synthesis of env gene products from the plasmid (pEV1/env 44-640) where the insert was placed in the wrong reading frame with respect to the initiator codon immediately downstream of the P1 promoter (Lane d). In this case, the E. coli containing these plasmids synthesized a 68 Kd protein in addition to the 35 Kd, 25 Kd and 18 Kd proteins. These results could be readily explained when the nucleotide sequence of the envelope gene (FIGS. 1A–1B) was examined. About 155 bases downstream to the KpnI site is an ATG codon which appeared to be utilized for the synthesis of env gene product by the two expression plasmids pEVI/env and pEV2/env 44-640. Internal translation initiation is also the likely explanation for the appearance of the 35 Kd, 25 Kd and 17 Kd proteins. Initiation codons which are preceded by so-called Shine-Dalgarno sequences (AGGA) are found within the env coding region at locations that are consistent with the sites of the observed protein products.

Figure 5:
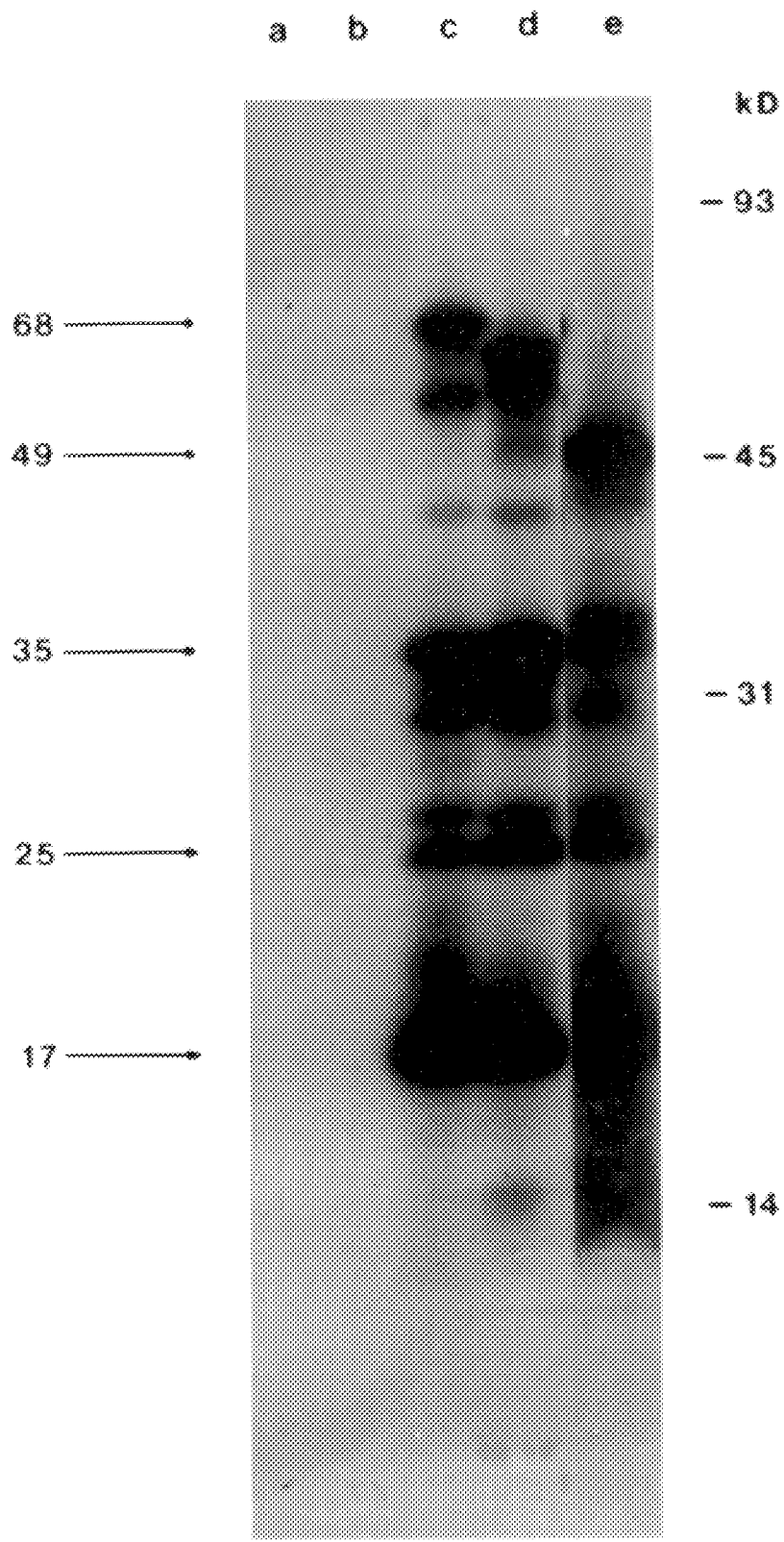
FIG. 5. Western blot analysis of env coded antigens produced in E. coli. Total bacterial proteins were resolved by SDS-PAGE, electro-blotted onto a nitrocellulose filter, and env encoded proteins were detected by reacting with human sera as described in Experimental Procedures: a) negative control, cells containing pJCL-E30 (p21T) induced at 42° C. for 2 hours; b) uninduced control, cells containing pEV3/env44-640 maintained at 30° C.; c) pEV3/env44-640; d) pEV1/env44-640; and e) pEV3/env205-640 induced at 42° C. for 2 hours.

To confirm the above interpretation and to rule out the possibilities that the smaller proteins are not formed as a result of premature termination or from proteolytic cleavage of the larger product, we constructed another deletion mutant in which sequences between the KpnI and StuI sites were deleted. This expression plasmid contains the coding sequences from amino acid positions 205–640 which could code for a protein of 49 Kd. Analysis of the proteins induced from E. coli harboring this plasmid verified that, in fact, these cells synthesize a 49 Kd protein in addition to the 35 Kd, 25 Kd and 17 Kd proteins (lane e, FIG. 5). From these results, we conclude that pEV3/env 44-640 expression plasmid directs the synthesis of a 68 Kd protein in addition to several additional smaller polypeptides (i.e., 35 Kd, 25 Kd and 17 Kd) produced from all of the env expression plasmids resulting from internal translation initiation within the env gene.

Screening of AIDS SERA

Figure 4A:
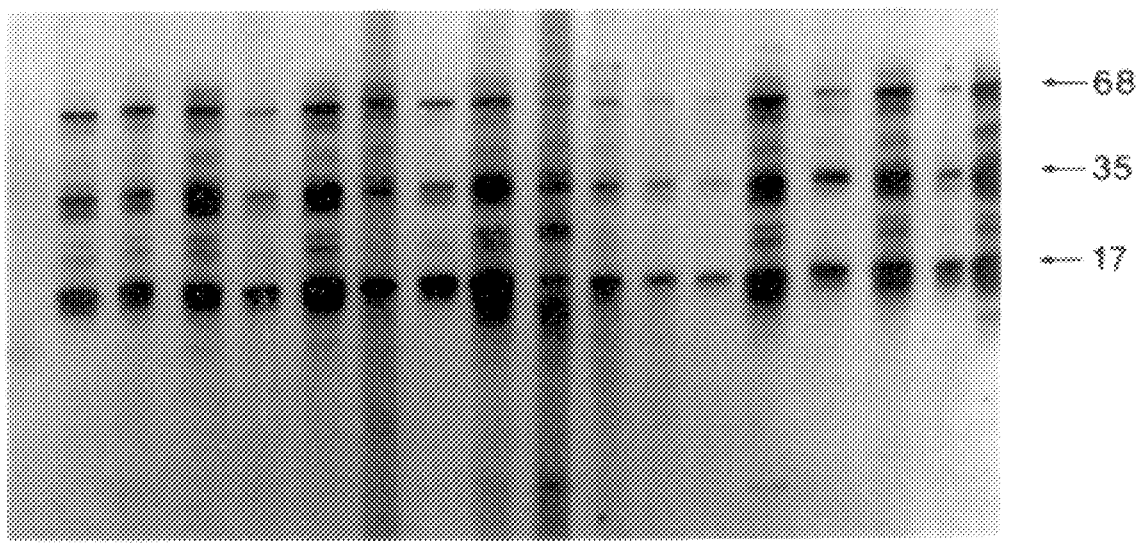
FIGS. 4A and 4B. Results of reacting the env gene proteins with 1000-fold diluted human sera and determining the presence of antigen-antibody complexes. Samples numbered 2, 3, 6, 8, 10, 12, 13, 14, 16, 17 and 18, 19 and 20 were blood samples of AIDS patients taken from all parts of the United States and Canada (FIG. 4B).
Figure 4B:
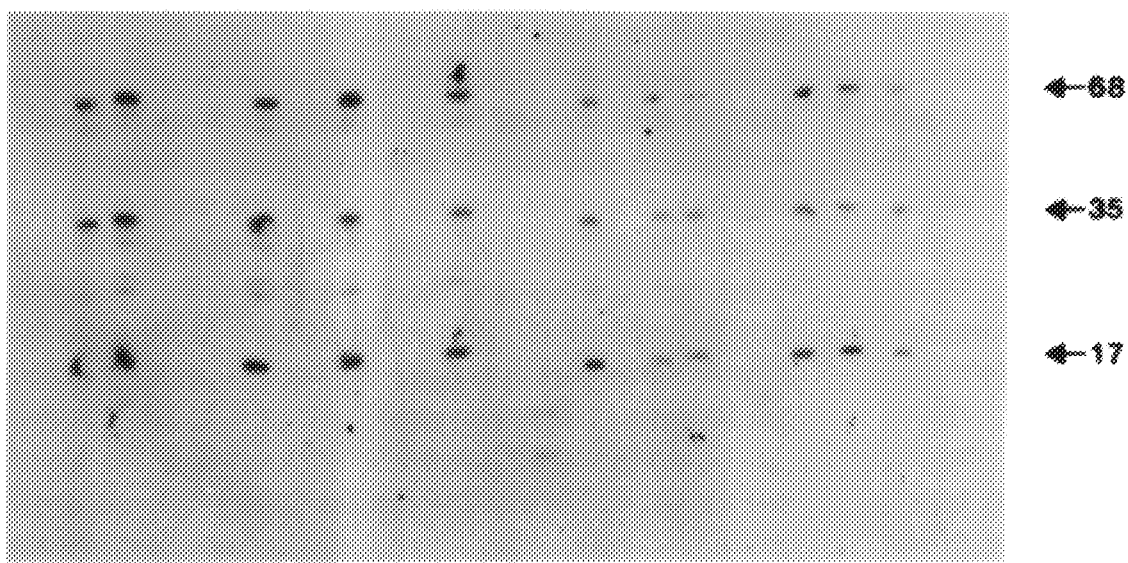

Because anti-HTLV-III antibodies are found in more than 90% of the AIDS patients, it was of interest to see if the bacterially synthesized env gene products could be used as diagnostic tools for the detection of these antibodies. For this analysis, total cell protein from an induced bacterial culture was fractionated by SDS-PAGE and transferred to a nitrocellulose filter by Western blotting technique. Strips of the filter containing transferred proteins were reacted with 1000-fold diluted human sera, and the antigen-antibody complexes formed were detected by incubation of the strips with 125-I-labelled Staphylococus aureus protein A followed by autoradiography. Prominent bands corresponding to reaction of the antibody to the 68 Kd, 35 Kd, 25 Kd and 17 Kd proteins were consistently observed when the serum used was from patients with AIDS syndrome. The results of one such assay with 18 human sera are presented in FIGS. 4A and 4B. The negative controls used were normal human sera and serum from a patient with HTLV-I infection. No reaction was observed with sera from healthy individuals or from HTLV-I infected individuals. The patient sera were derived from all parts of the United States including California and all AIDS patient sera tested so far were found to be positive. The results suggest that these antibodies are mainly directed against the protein back bone or the molecule.

It appears, therefore, that the env gene products constitute the best diagnostic reagents for the detection of AIDS associated antibodies. The env gene product of the instant invention encompasses a large portion of the protein molecule and contains both the conserved and divergent portions of the molecule. In spite of the divergence observed between HTLVIII and ARV-2 sequences the recombinant env proteins of the instant invention synthesized by the bacteria react with AIDS patient sera derived from both geographical locations of the United States. One hundred percent (100%) of AIDS patient sera (50 individual samples, 25 derived from the East Coast of the United States and 25 derived from California) tested showed high reactivity. This is strong evidence for the presence of conserved epitopes within the molecule against which the immune system could mount an antibody reaction. The human immune system may thus be mounting an immune response against conserved epitopes of the envelope molecule, as suggested by the reactivity of the AIDS patient sera. The observed divergence between various isolates of HTLV-III thus may not pose a problem for the use of recombinant protein as a vaccine. The 68 Kd protein is ideally suited for such a purpose since it encompasses a large portion of the gene product and has the unique structural feature of containing both the extracellular hydrophilic region and the membrane associated hydrophobic regions. This structural feature makes it well suited for encapsulation into liposomes which have been used as vehicles for vaccination against other vital envelope proteins.

Based on these discoveries it is proposed that in the practice of screening blood for acquired immune deficiency syndrome (AIDS) only AIDS envelope protein or a variant of said protein be utilized. Utilizing the env AIDS protein of the instant invention, human blood can be screened for the presence of antibodies to the AIDS virus. This and other techniques are readily determined, once, as taught for the first time by the present invention that the envelope AIDS protein is the envelope protein of the etiologic agent of AIDS. The foregoing and other objects, features and advantages of the invention will be apparent from the following examples of preferred embodiments of the invention.

EXAMPLE 1

Molecular Cloning and Nucleotide Sequence Analysis

The integrated proviral genome of HTLV-III was recently cloned frm the genomic DNA of H9 cells infected with HTLV-III (Shaw et al., supra, 1984). The proviral genome which was obtained by using XbaI digested H9/HTLV-III DNA contained two internal EcoRi sites within the viral genome and two additional sites in the cloning vector λ J1. These sites were used for further subcloning of the three DNA fragments of 5.5 Kbp, 4.5 Kbp and 1.1 Kbp into pBR322. Nucleotide sequence analysis of the proviral genome was determined by the chemical degradation method of Maxam and Gilbert, supra, (1980). For the sequence analysis, DNA inserts from the three subdlones were isolated by electroelution and further cleaved with appropriate restriction enzymes. The DNA fragments were labelled either with λ -32P-ATP and polynucleotide kinase at their 5' ends or with λ -32P-NTP, by filling with DNA polymerase (Klenow fragment), at their 3' ends. The DNA fragments labelled at the two ends were cleaved with a second enzyme and the fragments labelled at a single end were purified on 5% acrylamide gels and used for sequence analysis. For the sequence analysis of the env gene, a shotgun approach was utilized where the 4.5 EcoRI fragments were cleaved with one of the following enzymes: BglII, HindIII, XhoI, AvaII, HinfI and Sau3A and the restriction fragments labelled and sequenced as described above.

EXAMPLE 2

Construction of pEV/env 44-640

Expression plasmids pEV-vrf 1, 2, 3 have been described Lacal et al., Expression of Normal and Transforming H-ras Genes in *E.coli* and Purification of Their Encoded Proteins. Pro. Natl. Acad. Sci. USA 31, 5305–5309 (1984); Crowl, R. et al. Versatile Expression Vectors for High Level Synthesis of Cloned Gene Products in *E. coli*, Gene, in press.

pRC2 is a derivative of pBR322 containing a unique BGlII site adjacent (on the amp$^R$ side) to the EcoRI site in the plasmid. This plasmid was constructed in the following manner. 20 g of pBR322 plasmid DNA was digested with EcoRI and then split into two reactions. In one, the protruding 5' single-stranded termini were removed sith S1 nuclease; in the other reaction, the termini were filled-in by inorporating deoxynucleotides with the Klenow fragment of DNA polymerase I. Both reactions were terminated by phenol extraction followed by ethanol precipitation. Approximately 1 g of DNA from each reaction was mixed with 90 pmoles of phosphorylated BglII linkers (CAGATCTG, purchased from Collaborative Research) and incubated with T4 DNA ligase at 15° for 18 hours. The ligation products were then digested with BglII and PstI and subjected to gel electrophoresis in 1% agarose. The 3600 bp and 760 bp fragments from both reactions were recovered from the gel. For the construction of pRC2, the 3600 bp from the Klenow reaction was ligated to the 760 bp fragment from the S1 reaction. To construct a plasmid with the BglII site on the other side of EcoRI (tet$^R$ side), designated pRC1, the 3600 bp fragment from the S1 reaction was ligated to the 760 bp fragment from the Klenow reaction. *E. coli* strain RR1 was transformed with the ligation mixtures, and transformants were selected on LB agar plates containing 50 g/ml ampicillin. Transformants containing the expected plasmid constructions were identified by restriction analysis of the isolated plasmid DNA. DNA sequence analysis confirmed that the S1 nuclease treatment precisely removed the 5' single-stranded termini.

pRC23 (see FIG. 7) was constructed by inserting into pRC2 a 250 bp BglII-HaeIII fragment containing the λ $P_L$ promoter joined to a pair of complementary synthetic oligonucleotides comprising a model ribosome-binding site (RBS). The HaeIII site is located within the 5' non-coding region of the λ N gene 115 downstream of the $P_L$ transcriptional initiation site. Approximately 1 μg of a 450 bp BglII-HpaI fragment isolated from phage DNA was digested with HaeIII. 200 ng of the resulting digestion products were mixed with 60 pmoles each of phosphorylated synthetic oligonucleotides containing the model RBS. The ligated molecules were digested with BglII and EcoRI and separated on a 5% polyacrylamide gel. The 270 bp ligation product was recovered from the gel, mixed with gel purified pRC2 vector that had been digested with BGlII and EcoRI, and incubated with T4 DNA ligase at 15° for 15 hours. The ligation mixture was used to transform strain RR1 (pRK248cIts). Transformants selected on ampicillin-containing medium were screened by restriction analysis of the isolated plasmid DNA. The expected plasmid construction, pRC23, was confirmed by further restriction enzyme digestons and by DNA sequence analysis across the EcoRI junction (FIG. 7).

Figure 8:
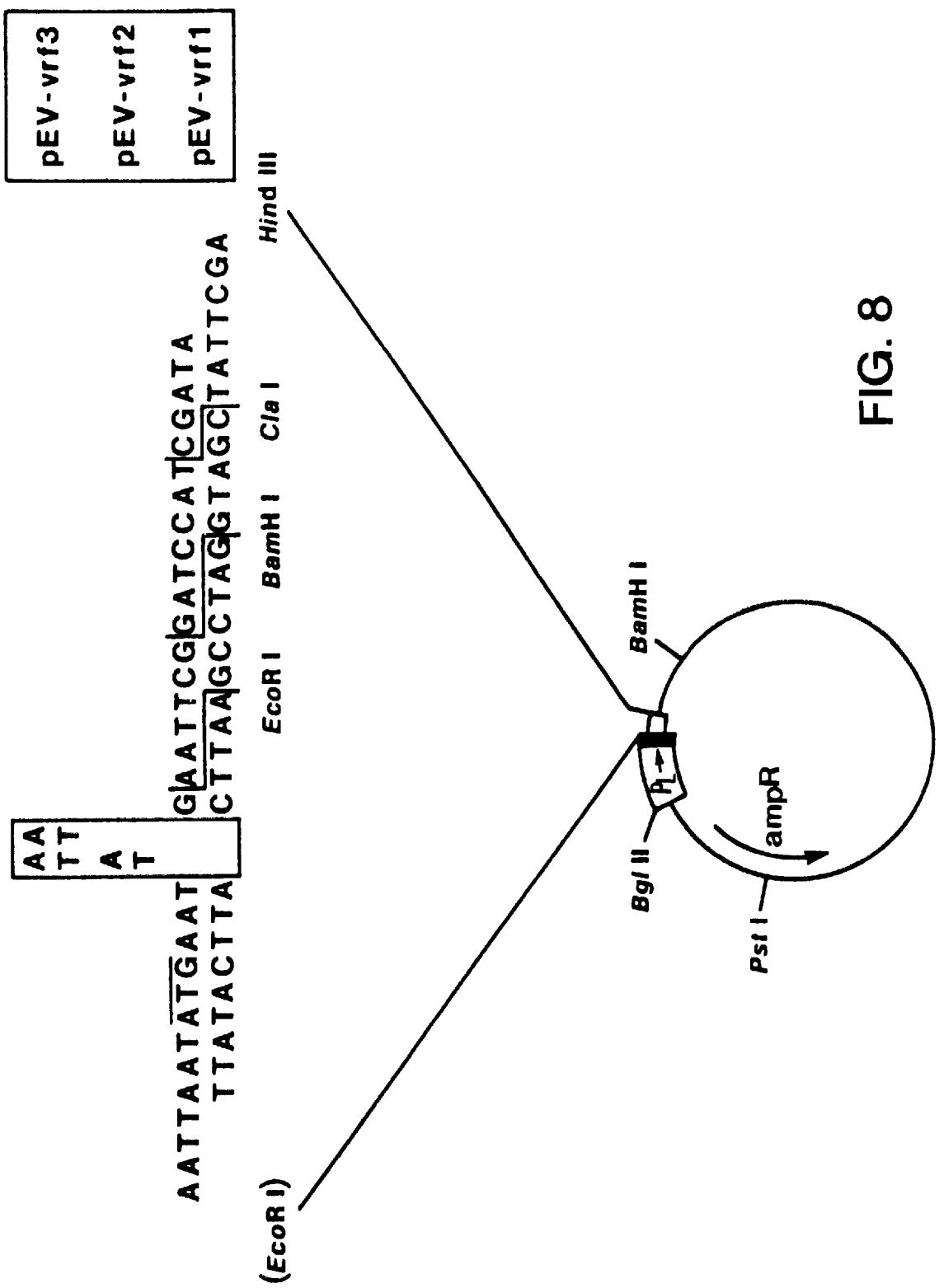
FIG. 8. Enlargement of the pEV/env 44-640 variable reading frame (vrf) expression plasmids as shown in FIG. 3 and described in Examples 2 and 3. The structure and pertinent sequences of the pEV-vrf plasmids are shown. The solid black region represents the synthetic ribosome binding site sequences upstream of the ATG initiation codon (overlined).

For the construction of the pEV-vrf set of plasmids (see FIG. 8), pRC23 was digested with EcoRI and HindIII and isolated by preparative agarose gel electrophoresis. The mixture of synthetic oligonucleotides (32, 33, and 34 nucleotides) was combined with the mixture of the complementary sequences, heated to 58° for 5 minutes in 150 mM NaCl, and cooled slowly to allow annealing. 0.1 pmoles of the synthetic duplexes were added to 0.07 pmoles of the pRC23/EcoRI-HindIII vector and incubated with T4 DNA ligase at 15° for 15 hours. Strain RR1 (λcI857) was transformed with the ligation products. Six ampicillin resistant transformants were selected for DNA sequence analysis. Of the six, two contained the expected sequence for pEV-vrf1, one for pEV-vrf2, and three for pEV-vrf3 (FIG. 3).

For the expression of the AIDS env gene, one μg of a 2400 bp EcoRI-HindIII DNA fragment, which was isolated from the cloned HTLV-III proviral genome by preparative agarose gel electrophoresis, was mixed with 0.1 g of EcoRI-HindIII digested vector DNA (pEV-vrf 1, 2, or 3). After heating at 65° C. for 3 minutes, the mixtures were chillled on ice, and 20 μl ligation reactions were assembled which contained 50 mM Tris-HCl (pH 7.4), 10 mM MgCl$_2$, 10 mM DTT, 0.3 mM ATP, and 200 units of T$_4$ DNA ligase. After incubation at 15° C. for 4 hours, the reactions were terminated by heating at 65° C. for 5 minutes. The ligation products were used to transform *E. coli* strain MC1061 (pRK248cIts). Transformants were selected on Luria broth agar containing 50 μg/ml ampicillin at 30° C. for 18 hours. Plasmid DNA was isolated from 1 ml of each culture and subjected to restriction analysis. All 12 isolates contained the expected plasmid construction. These intermediate constructions were then used to make pEV1, 2, and 3/env 44-640 by deleting the 600 bp between the EcoRI and KPnI sites as described below.

Approximately 0.5 μg of plasmid DNA was digested with KPNI and EcoRI. The resulting termini were then treated with the Klenow fragment of DNA polymerase I in the presence of all four deoxyribonucleotides at (100 μM) at 37° C. for 30 minutes. This step results in the "filling-in" of the 5' overhang of the EcoRI terminus and the removal of the 3' overhang of the KpnI terminus. Upon recirculization of the linear plasmid and blunt-end ligation of these termini, an EcoRI site is regenerated. Transformants containing plasmids with the expected deletion were identified by restriction analysis.

A second set of deletion derivatives, designated pEV/env 205-640 was constructed in a similar fashion. A portion of the linear plasmid that had been digested with EcoRI and KpnI and treated with Klenow, as described above, was further digested with StaI. Again, upon recircularization and blunt-end ligation, the EcoRI site was regenerated; however, an additional 483 bp of env coding sequences were removed.

EXAMPLE 3

Expression Plasmids

Expression plasmids pEV-vrf 1,2, 3 have been described (Lacal et al., supra, 1984; Crowl et al., supra, 1985), for the expression of the HTLV-III evelope gene, a 2400 bp EcoRI- HindIII fragment was inserted into the three expression vectors between the EcoRI and HindIII sites (FIG. 3). This intermediate construct was then cleaved with EcoRI and KpnI and the vector DNA purified from the 600 bp fragment by agarose gel electrophoresis. The DNA fragment was then treated with the Klenow fragment of *E. coli* DNA polymerase I and recircularized using the T4 ligase. Cultures of *E. coli* strain MC 1061 transformed with pRK248cIts and the pEV 1,2, or 3/env plasmids were grown in M9medium at 30° C. to mid-log phase and then induced by shifting to 42° C. for 2 hr.

EXAMPLE 4

Expression and Purification of Env AIDS

A homogeneous recombinant viral env AIDS was purified according to the following procedure. The env AIDS protein expressed by a microbe tends to associate with the membrane fractions of the host microbe, principally the inner membrane of the microbe. The following purification method was designed to deal with this finding.

This purification method comprises:
(a) lysis of transformed microbial cells producing recombinant env AIDS protein;
(b) separation of env AIDS associated cellular membranes from other cellular components;
(c) extraction of env AIDS from associated membranes; and
(d) chromatographic purification of the resultant extraction solution containing env AIDS to yield a substantially pure recombinant viral env protein.

More specifically, the preferred purification method for the preparation of substantially pure recombinant viral env protein comprises:
(a) cultivating a transformed organism containing a DNA sequence which codes for viral env protein;
(b) causing a culture of the transformed organism of step (a) to accumulate the env protein;
(c) lysing the culture of transformed organisms of step (b) to form a cell lysate mixture;
(d) isolating the cell membrane components of the cell lysate mixture of step (c);
(e) washing the isolated cell membrane components with an extraction solution to yield a wash solution containing env protein; and
(f) chromatographically purifying the wash solution of step (e) to yield a substantially pure env AIDS protein.

In carrying out this method it is preferred that the cells be lysed by sonification, although it is forseeable that other known methods such as enzyme or mechanical lysis could also be used. It is preferred that the cell membrane component, specifically the inner and outer membranes, be isolated from other cellular components by methods such as centrifugation. It has been found that env AIDS expressed by the transformed microorganism tends to become associated with the cellular membranes. Therefore, isolation of these membranes during the purification process ensures high purification levels and high purity env AIDS at the end of the purification procedure.

Once the cell membranes are isolated from the lysate mixture, they are washed with an extraction solution, preferably salt solutions and a detergent to yield a second solution containing approximately 50% env AIDS protein. Preferably the cell membranes are washed in four separate steps with the salt solutions and detergent although it is forseeable that certain of these steps could be combined, rearranged or eliminated. The first step of washing the cell membrane may be done with a salt solution, preferably 1M NaCl. In the second step the cell membrane is washed with a detergent solution, preferably 1% Triton X-100. In the third step, the cell membrane is washed with another salt solution, 1.75M to 3.5M Guanidine HCl. The final wash is also with a salt solution preferably about 7M Guanidine HCl. The wash solution which results from the fourth and final wash comprises about 50% env AIDS.

The final 50% env AIDS wash solution is then further purified by a chromatography step, preferably reverse phase high performance liquid chromatography (HPLC). The HPLC step yields env AIDS protein in a substantially 100% pure form. It is also foreseeable that monoclonal antibody affinity chromatography columns utilizing env AIDS polyclonal or monoclonal antibodies, could be used as an alternative to HPLC.

EXAMPLE 6

Polyacrylamide Gel Electrophoresis and Western Blot Analysis

Cells were lysed by resuspending the cell pellets (approximately $10^8$ cells) in TG buffer (10 mM Tris, pH 7.4. 10% glycerol), mixed with an equal volume of 2× sample buffer of Laemmli (Laemmli, U.K., Cleavage of Structural Proteins During the Assembly of the Head of Bacteriophage T4, Nature 227, 680–685, 1970) and incubated at 95° C. for five (5) minutes. Debris was pelleted by centrifugation and the cleared lystes were subjected to SDS-PAGE analysis, Id. For Western blot analysis, the proteins from the acrylamide gel were electroblotted onto a 0.1 μm nitrocellulose membrane (Schleicher and Schuell) for 16 hr at 50 V, in 12.5 mM Tris, 96 mM glycine, 20% methanol, 0.01% SDS at pH 7.5. Processing of the blot was carried out using the methods described by Towbin et al. Electrophoretic Transfer of Proteins From Polyacrylamide Gels to Nitrocellulose Sheet: Procedure and Some Applications, Proc. Natl. Acad. Sci. U.S.A., 76, 4350–4354, (1979). For treatment with the human sera, the blots were incubated with a 1000 fold dilution of the sera in antibody buffer (20 mM sodium phosphate buffer, pH 7.5 containing 0.5M NaCl, 1% BSA and 0.05% Tween 20) for 2–6 hr. The blots were then washed twice with phosphate buffered saline containing 0.05% Tween 20 and then incubated with 125-I-labelled *Staphylococous aureus* protein A for an additional period of 1 hr. The blot was then washed twice in PBS-Tween 20 buffer, dried and autoradiographed.

EXAMPLE 7

Immunization with Env Protein of AIDS Virus

It is clear that in spite of the divergence observed between HTLVIII and ARV-2 sequences, the recombinant proteins synthesized by the bacteria react well with AIDS patient sera derived from both geographical locations of the United States. One hundred percent (100%) of the AIDS patient sera tested showed high reactivity (50 individual samples, 25 from the east coast of the United States and 25 from the west coast of the United States). Thus all the env proteins contain at least one conserved epitope. All of the human sera from AIDS patients tested contained antibodies to the env proteins of the instant invention. This strongly suggests that these env proteins with the conserved epitopes would be immunogenic in man.

It will be readily appreciated that the env proteins of the instant invention can be incorporated into vaccines capable of inducing protective immunity against the AIDS virus. By methods known in the art, the specific amino acids conprising the epitopes of the env protein may be determined. Peptides may then be synthesized, comprising an amino acid sequence corresponding to an epitope of an env AIDS protein either in monomeric or multimeric form. These synthetic peptides may then be incorporated into vaccines capable of inducing protective immunity aggainst AIDS virus. Techniques for enhancing the antigenicity of such repeated peptides include incorporation into a multimeric structure, binding to a highly immunogenic protein carrier, for example, keyhold limpet hemocyanin, or diptheria toxoid, and administration in combination with adjuvants or any other enhancers of immune response. In addition, the vaccine composition may comprise antigens to provide immunity against other diseases in addition to AIDS.

An amino acid sequence corresponding to an epitope of a env protein (repeated peptide) may be obtained by chemical synthetic means or by purification from biological sources including genetically modified microorganisms or their culture media. The repeated peptide may be combined in an amino acid sequence with other peptides including fragments of other proteins, as for example, when synthesized as a fusion protein, or linked to other antigenic or non-antigenic peptides of synthetic or biological origin. The term "corresponding to an epitope of a env protein" will be understood to include the practical possibility that, in some instances, amino acid sequence variations of a naturally occurring repeated peptide may be antigenic and confer protective immunity against AIDS infection. Possible sequence variations include, without limitation, amino acid substitutions, extensions, deletions, interpolations and combinations thereof. Such variations fall within the contemplated scope of the invention provided the peptide containing them is antigenic and antibodies elicited by such peptide cross-react with naturally occurring env protein or non-variant repeated peptides of env protein, to an extent sufficient to provide protective immunity when administered as a vaccine. Such vaccine compositions will be combined with a physiologically acceptable medium. The size and shape of epitopes found in carbohydrate antigens have been extensively studied, but less is known about the structure of epitopes from protein molecules. Some epitopes of protein antigens have been defined at the level of their tertiary structure. In every instance, the epitopes were formed not by the primary sequences alone, but by the juxtaposition of residues brought together by the folding of the polypeptide chain(s) of the native molecule. In addition, the structure of the 68 Kd env protein of the instant invention makes it particularly well suited for use as a vaccine. The 68 Kd env protein comprises a large portion of the gene product which: was shown to be reactive with all the AIDS sera tested; and, has the unique structural feature of containing both an extracellular hydrophilic region and the transmembrane hydrophobic regions. The latter structural feature makes it well suited for use as a vaccine using liposome encapsulation to create a vehicle for administration.

Routes of administration, antigen dose, number and frequency of injections are all matters of optimization within the scope of ordinary skill in the art, particularly in view of the fact that there is experience in the art in providing protective immunity by the injection of other related antigens to provide immunity in other viral infections. It is anticipated that the principal value of providing immunity to AIDS infection will be for those individuals who have had no previous exposure to AIDS, e.g., individuals who are in the high risk population, such as homosexuals, drug addicts and people from Haiti and Central America and individuals who may be receiving blood transfusions. It is also anticipated that temporary immunity for infants may be provided by immunization of mothers during pregnancy.

EXAMPLE 8

Diagnostic Test for AIDS

It is clear that the env gene proteins of the instant invention may be used as diagnostic reagents for the detection of AIDS-associated antibodies. It is also apparent to one of ordinary skill that a diagnostic assay for AIDS using polyclonal or monoclonal antibodies to the AIDS env protein of the instant invention may be used to detect the presence of the AIDS virus in human blood. In one embodiment a competition immunoassay is used where the antigenic substance, in this case the AIDS virus, in a blood sample competes with a known quantity of labelled antigen, in this case labelled AIDS env protein, for a limited quantity of antibody binding sites. Thus, the amount of labelled antigen bound to the antibody is inversely proportional to the amount of antigen in the sample. In another embodiment, an immunometric assay may be used wherein a labelled AIDS-env antibody is used. In such an assay, the amount of labelled antibody which complexes with the antigen-bound antibody is directly proportional to the amount of antigen (AIDS virus) in the blood sample. In a simple yes/no assay to determine whether the AIDS virus is present in blood, the solid support is tested to detect the presence of labelled antibody. In another embodiment, monoclonal antibodies to AIDS env protein may be used in an immunometric assay. Such monoclonal antibodies may be obtained by methods well known in the art, particularly the process of Milstein and Kohler reported in Nature 256, 495–497 (1975).

The immunometric assay method is as follows: Duplicate samples are run in which 100 $\mu$l of a suspension of antibody immobilized on agarose particles is mixed with 100 $\mu$l of serum and 100 $\mu$l of soluble $^{125}$I-labelled antibody. This mixture is for specified times ranging from one quarter hour to twenty four hours. Following the incubation periods the agarose particles are washed by addition of buffer and then centrifuged. After removal of the washing liquid by aspiration, the resulting pellet of agarose particles is then counted for bound $^{125}$I-labelled antibody. The counts obtained for each of the complexes can then be compared to controls.

While the invention has been described in terms of certain preferred embodiments, modifications obvous to one with ordinary skill in the art may be made without departing from the scope of the invention. For example, it is understood that the env AIDS DNAs described herein represent only the precise structure of two naturally occurring gene segments. It is expected that slightly modified alleles will be found encoding for similarly functioning proteins, and such gene segments and proteins are considered to be equivalents for the purpose of this invention. It is also suspected that other variants in addition to those described herein will be found and that the envelope protein of said variants will differ slightly. These variant envelope proteins are likewise considered within the scope of the invention. DNA having equivalent codons is considered within the scope of the invention, as are synthetic gene segments that encode homologous proteins of the viral envelope.

Various features of the invention are set forth in the following claims.

What is claimed is:

1. An expression vector comprising (i) an isolated HIV polynucleotide sequence encoding an HIV envelope polypeptide, said polynucleotide having the following nucleotide sequence:

GTGTGGAAGGAAGCA ACCACCACTCTATTTTG-TGCATCAGATGCTAAAGCATATGATACAGAGG-TACATAATGTTTGGGCCACA CATGCCTGTACC-CACAGACCCCAACCCACA AGAAGTAGTATTG-GTAAATGTGACAGAAATT TTAAC ATGTGGAA-AAATGACATGGTAGAACA- GATGCATGAGGA-TATAATCAGTTTATGGGATC AAAGCCTAAAG CCATGTGTAAAATTAACCCC ACTCTGTGTTAG-TTTAAAGTGCACTGATT TGA AGAATGATACT-AATACC AATAGTAGTAGCGGGAGAATGATAA-TGGAGAAAGGAGAGATAAAAAACTGCTCTTT-CAATATCAGCACA AGCATAAGAGGTAAGGTG-CAGAAAGAATATGCATTTTTTTATAAACTTGAT-ATAATACCAATAGATAAT GATACTACCAGCTAT-ACGTTGACAAGTTGTAACACCTCAGTCATTAC-ACAGGCCTGTCCAAAGGTATCC TTTGAGCCA-ATTCCCATACATTATTGTGCCCCGGCTGGTTTT-GCGATTCTAAAATGTAATAATAAGACG TTCAA-TGGAACAGGACCATGTACAAATGTCAGCACA-GTACAATGTACACATGGAATTAGGCCAGTAGTA TCAACTCAACTGCTGTTAAATGGCAGTCTAGC-AGAAGAGAGGTAGTAATTAGATCTGTCAATTT-CACG GACAATGCTAAAACCATAATAGTACAG-CTGAACACATCTGTAGAAATTAATTGTACAAG-ACCCAACAAC AATACAAGAAAAAAATCCGT-ATCCAGAGGGGACCAGGGAGAGCATTTGTTA-CAATAGGAAAATAGGA AATATGAGACAAGC-ACATTGTAACATTAGTAGAGCAAAATGGAATG-CCACTTTAAAACAGATAGCTAGC AAATTAAG-AGAACAATTTGGAAATAATAAAACAATAATCT-TTAAGCAATCCTCAGGAGGGGACCCAGAA AT-TGTAACGCACAGTTTTAATTGTGGAGGGGAAT-TTTTCTACTGTAATTCAACACAACTGTTTAATA-GT ACTTGGTTTAATAGTACTTGGAGTACTGAA-GGGTCAAATAACACTGAAGGAAGTGACACAA-TCACACTC CCATGCAGAATAAAACAATTTATA-AACATGTGGCAGGAAGTAGGAAAAGCAATGT-ATGCCCCTCCCATC AGCGGACAAATTAGATG-TTCATCAAATATTACAGGGCTGCTATTAACAA-GAGATGGTGGTAATAACAAC AATGGGTCCGA-GATCTTCAGACCTGGAGGAGGAGATATGAGG-GACAATTGGAGAAGTGAATTATATAAA TATAA-AGTAGTAAAAATTGAACCATTAGGAGTAGCAC-CCACCAAGGCAAAGAGAAGAGTGGTGCAGA-GA GAAAAAAGAGCAGTGGGAATAGGAGCTT-TGTTCCTTGGGTTCTTGGGAGCAGCAGGAAG-CACTATGGGC GCAGCGTCAATGACGCTGACG-GTACAGGCCAGACAATTATTGTCTGGTATAGT-GCAGCAGCAGAACAAT TTGCTGAGGGCTATT-GAGGCGCAACAGCATCTGTTGCAACTCACAG-TCTGGGGCATCAAGCAGCTCCAG GCAAGAAT-CCTGGCTGTGGAAAGATACCTAAAGGATCAA-CAGCTCCTGGGGATTTGGGGTTGCTCTGGA AAACTAATTTGCACCACTGCTGTGCCTTGGAA-TGCTAGTTGGAGTAATAAATCTCTGGAACAGA-TTTGG AATCACACGACGTGGATGGAGTGGGA-CAGAGAAATTAACAATTACACAAGC and (ii) a plasmid having an insertion site into which said polynucleotide sequence is inserted, said insertion site being downstream of a promoter sequence for transcription, translation and expression of said HIV envelope polypeptide in a host cell, said HIV polynucleotide sequence and its encoded amino acid sequence having homology with envelope sequences of related human immunodeficiency viruses.

2. An expression vector comprising (i) an isolated HIV polynucleotide sequence encoding an HIV envelope polypeptide, said polynucleotide having the following nucleotide sequence:

TGTCCAAGGTATCC TTTGAGCCAATTCCCATAC-ATTATTGTGCCCCGGCTGGTTTTGCGATTCTAA-AATGTAATAATAAGACG TTCAATGGAACAGGA-CCATGTACAAATGTCAGCACAGTACAATGTAC-ACATGGAATTAGGCCAGTAGTA TCAACTCAAC-TGCTGTTAAATGGCAGTCTAGCAGAAGAAGAG-GTAGTAATTAGATCTGTCAATTTCACG GACAA-TGCTAAAACCATAATAGTACAGCTGAACACAT-CTGTAGAAATTAATTGTACAAGACCCAACAAC AATACAAGAAAAAAATCCGTATCCAGAGGGG-ACCAGGGAGAGCATTTGTTACAATAGGAAAA-TAGGA AATATGAGACAAGCACATTGTAACATT-AGTAGAGCAAAATGGAATGCCACTTTAAAACA-GATAGCTAGC AAATTAAGAGAACAATTTGGAA-ATAATAAAACAATAATCTTTAAGCAATCCTCAG-GAGGGGACCCAGAA ATTGTAACGCACAGTTT-TAATTGTGGAGGGGAATTTTTCTACTGTAATTC-AACACAACTGTTTAATAGTACTTGGTTTAATAG-TACTTGGAGTACTGAAGGGTCAAATAACACTG-AAGGAAGTGACACAATCACACTC CCATGCAG-AATAAAACAATTTATAAACATGTGGCAGGAAG-TAGGAAAAGCAATGTATGCCCCTCCCATC AGC-GGACAAATTAGATGTTCATCAAATATTACAGG-GCTGCTATTAACAAGAGATGGTGGTAATAACA-AC AATGGGTCCGAGATCTTCAGACCTGGAGG-AGGAGATATGAGGGACAATTGGAGAAGTGAAT-TATATAAA TATAAAGTAGTAAAAATTGAACCAT-TAGGAGTAGCACCCACCAAGGCAAAGAGAAG-AGTGGTGCAGAGA GAAAAAAGAGCAGTGGG-AATAGGAGCTTTGTTCCTTGGGTTCTTGGGAGT-CAGCAGGAAGCACTATGGGC GCAGCGTCAAT-GACGCTGACGGTACAGGCCAGACAATTATTGT-CTGGTATAGTGCAGCAGCAGAACAAT TTGCT-GAGGGCTATTGAGGCGCAACAGCATCTGTTGC-AACTCACAGTCTGGGGCATCAAGCAGCTCCAG GCAAGAATCCTGGCTGTGGAAAGATACCTAAA-GGATCAACAGCTCCTGGGGATTTGGGGTTGCT-CTGGA AAACTAATTTGCACCACTGCTGTGCCT-TGGAATGCTAGTTGGAGTAATAAATCTCTGGAA-CAGATTTGG AATCACACGACGTGGATGGAGT-GGGACAGAGAAATTAACAATTACACAAGC and (ii) a plasmid having an insertion site into which said polynucleotide sequence is inserted, said insertion site being downstream of a promoter sequence for transcription, translation and expression of said HIV envelope polypeptide in a host cell, said HIV polynucleotide sequence and its encoded amino acid sequence having homology with envelope sequences of related human immunodeficiency viruses.

3. An expression vector comprising (i) an isolated HIV polynucleotide sequence encoding an HIV envelope polypeptide, said polynucleotide having the following nucleotide sequence:

ATGAGACAAGCACATTGTAACATTAGTAGAGCA-AAATGGAATGCCACTTTAAAACAGATAGCTA GCAAATTAAGAGAACAATTTGGAAATAATAAA-ACAATAATCTTTAAGCAATCCTCAGGAGGGGA-CCCAGAA ATTGTAACGCACAGTTTTAATTGTG-GAGGGGAATTTTTCTACTGTAATTCAACACAA-CTGTTTAATAGT ACTTGGTTTAATAGTACTTGG-AGTACTGAAGGGTCAAATAACACTGAAGGAA-GTGACACAATCACACTCCCATGCAGAATAAAA-

CAATTTATAAACATGTGGCAGGAAGTAGGAAA-AGCAATGTATGCCCCTCCCATC AGCGGACAA-ATTAGATGTTCATCAAATATTACAGGGCTGCTA-TTAACAAGAGATGGTGGTAATAACAACAATGG-GTCCGAGATCTTCAGACCTGGAGGAGGAGATA-TGAGGGACAATTGGAGAAGTGAATTATATAAA TATAAGTAGTAAAAATTGAACCATTAGGAGTAG-CACCCACCAAGGCAAAGAGAAGAGTGGTGC-AGAGA GAAAAAAGAGCAGTGGGAATAGGAG-CTTTGTTCCTTGGGTTCTTGGGAGCAGCAGGA-AGCACTATGGGC GCAGCGTCAATGACGCTGA-CGGTACAGGCCAGACAATTATTGTCTGGTATAG-TGCAGCAGCAGAACAAT TTGCTGAGGGCTAT-TGAGGCGCAACAGCATCTGTTGCAACTCACAG-TCTGGGGCATCAAGCAGCTCCAG GCAAGAAT-CCTGGCTGTGGAAAGATACCTAAAGGATCAAC-AGCTCCTGGGGATTTGGGGTTGCTCTGGAAAA-CTAATTTGCACCACTGCTGTGCCTTGGAATGCT-AGTTGGAGTAATAAATCTCTGGAACAGATTTGG AATCACACGACGTGGATGGAGTGGGACAGAG-AAATTAACAATTACACAAGC and (ii) a plasmid having an insertion site into which said polynucleotide sequence is inserted, said insertion site being downstream of a promoter sequence for transcription, translation and expression of said HIV envelope polypeptide in a host cell, said HIV polynucleotide sequence and its encoded amino acid sequence having homology with envelope sequences of related human immunodeficiency viruses.

4. An expression vector comprising (i) an isolated HIV polynucleotide sequence encoding an HIV envelope polypeptide, said polynucleotide having the following nucleotide sequence:

ATGTATGCCCCTCCCATC AGCGGACAAATTAGAT-GTTCATCAAATATTACAGGGCTGCTATTAACAA-GAGATGGTGGTAATAACAAC AATGGGTCCGA-GATCTTCAAACTGGAGGAGGAGATATGAGGGA-CAATTGGAGAAGTGAATTATATAAAA TATAAAG-TAGTAAAAATTGAACCATTAGGAGTAGCACCC-ACCAAGGCAAAGAGAAGAGTGGTGCAGAGA GAAAAAAGAGCAGTGGGAATAGGAGCTTTGT-TCCTTGGGTTCTTGGGAGCAGCAGGAAGCACT-ATGGGC GCAGCGTCAATGACGCTGACGGTAC-AGGCCAGACAATTATTGTCTGGTATAGTGCAG-CAGCAGAACAAT TTGCTGAGGGCTATTGAGG-CGCAACAGCATCTGTTGCAACTCACAGTCTGG-GGCATCAAGCAGCTCCAG GCAAGAATCCTGG-CTGTGGAAAAGTACCTAAAGGATCAACAGCTC-CTGGGGATTTGGGGTTGCTCTGGA AAACTAAT-TTGCACCACTGCTGTGCCTTGGAATGCTAGTTG-GAGTAATAAATCTCTGGAACAGATTTGG AATC-ACACGACGTGGATGGAGTGGGACAGAGAAAT-TAACAATTACACAAGC and (ii) a plasmid having an insertion site into which said polynucleotide sequence is inserted, said insertion site being downstream of a promoter sequence for transcription, translation and expression of said HIV envelope polypeptide in a host cell, said HIV polynucleotide sequence and its encoded amino acid sequence having homology with envelope sequences of related human immunodeficiency viruses.

5. An expression vector comprising (i) an isolated HIV polynucleotide sequence encoding an HIV envelope polypeptide, said polynucleotide having the following nucleotide sequence:

ATGAGGGACAATTGGAGAAGTGAATTATATAAA TATAAAGTAGTAAAAATTGAACCATTAGGAGT-AGCACCCACCAAAAGGCAAGAGAGAGTGGTG-CAGAGA GAAAAAAGAGCAGTGGGAATAGGA-GCTTTGTTCCTTGGGTTCTTGGGAGCAGCAGG-AAGCACTATGGGC GCAGCGTCAATGACGCTG-ACGGTACAGGCCAGACAATTATTGTCTGGTAT-AGTGCAGCAGCATAACAATTTGCTGAGGGCT-ATTGAGGCGCAACAGCATCTGTTGCAACTCA-CAGTCTGGGGCATCAAGCAGCTCCAG GCAA-GAATCCTGGCTGTGGAAAGATA CCTAAAGG-ATCAACAGCTCCTGGGGATTTGGGGTTGCTC-TGGA AAACTAATTTGCACCACTGCT-GTGCCTTGGAATGCTAGTTGGAGTAATAAATCT-CTGGAACAGAITGG AATCACACGACGTGGAT-GGAGTGGGACAGAGAAATTAACAATTACACA-AAGCT and (ii) a plasmid having an insertion site into which said polynucleotide sequence is inserted, said insertion site being downstream of a promoter sequence for transcription, translation and expression of said HIV envelope polypeptide in a host cell, said HIV polynucleotide sequence and its encoded amino acid sequence having homology with envelope sequences of related human immunodeficiency viruses.

6. A host cell transformed with the expression vector of claim 1.

7. A host cell transformed with the expression vector of claim 2.

8. A host cell transformed with the expression vector of claim 3.

9. A host cell transformed with the expression vector of claim 4.

10. A host cell transformed with the expression vector of claim 5.

11. An isolated HIV envelope polynucleotide having the nucleotide depicted in FIG. 1.

12. An isolated HIV envelope polynucleotide having the nucleotide depicted in claim 1.

13. An isolated HIV envelope polynucleotide having the nucleotide depicted in claim 2.

14. An isolated HIV envelope polynucleotide having the nucleotide depicted in claim 3.

15. An isolated HIV envelope polynucleotide having the nucleotide depicted in claim 4.

16. An isolated HIV envelope polynucleotide having the nucleotide depicted in claim 5.

17. An expression vector comprising (i) an isolated HIV polynucleotide sequence encoding an HIV envelope polypeptide having amino acid residues 44 to 640 of the HIV envelope protein; and (ii) a plasmid having an insertion site into which said polynucleotide sequence is inserted, said insertion site being downstream of a promoter sequence for transcription, translation and expression of said HIV envelope polypeptide in a host cell, wherein said expression vector produces HIV envelope expression products having molecular weights of about 68 Kd, 35 Kd, 25 Kd and 17–18 Kd as determined by gel electrophoresis.

18. The expression vector according to claim 17, wherein said HIV polynucleotide sequence encoding said HIV envelope polypeptide is a KpnI to HindIII restriction fragment of proviral HIV genomic DNA.

19. The expression vector according to claim 17 or 18, wherein said HIV envelope expression products immunoreact with sera from AIDS patients.

20. The expression vector according to claim 17, wherein said HIV envelope expression product has a molecular weight of 68 Kd and immunoreacts with sera from AIDS patients.

21. An expression vector comprising (i) an isolated HIV polynucleotide sequence encoding an HIV envelope polypeptide having amino acid residues 205 to 640 of the HIV envelope protein and (ii) a plasmid having an insertion site into which the polynucleotide sequence is inserted, said insertion site being downstream of a promoter sequence for transcription, translation and expression of the HIV envelope polypeptide in a host cell, wherein said expression vector produces HIV envelope expression products having molecular weights of about 49 Kd, 35 Kd, 25 Kd and 17–18 Kd as determined by gel electrophoresis.

22. The expression vector according to claim 21, wherein said HIV expression products immunoreact with sera from AIDS patients.

23. A host cell transformed with said expression vector according to claim 17 or claim 20.

24. The transformed host cell according to claim 23 being one selected from eucaryotic or procaryotic cells.

25. The transformed host cell of claim 23 which is a procaryote *Escherichia coli*.

26. A method of producing immunoreactive envelope polypeptides of HIV, comprising:
   (a) transforming a host cell with the expression vector according to claim 17 or claim 21;
   (b) culturing said host cell under conditions allowing for the expression of HIV envelope polypeptides; and
   (c) isolating said expressed HIV envelope polypeptides.

* * * * *